United States Patent
Cammish et al.

(10) Patent No.: US 10,117,997 B2
(45) Date of Patent: Nov. 6, 2018

(54) DISPENSING MECHANISM FOR A MEDICAL DEVICE

(71) Applicant: NORTON HEALTHCARE LIMITED, Castleford, Yorkshire (GB)

(72) Inventors: Neil Cammish, Salford (GB); Mark Horlock, Timperley (GB)

(73) Assignee: Norton Healthcare Limited, Castleford (GB)

(*) Notice: Subject to any disclaimer, the term of this patent is extended or adjusted under 35 U.S.C. 154(b) by 0 days.

(21) Appl. No.: 14/776,226

(22) PCT Filed: Mar. 14, 2014

(86) PCT No.: PCT/EP2014/055130
§ 371 (c)(1),
(2) Date: Sep. 14, 2015

(87) PCT Pub. No.: WO2014/140294
PCT Pub. Date: Sep. 18, 2014

(65) Prior Publication Data
US 2016/0038686 A1 Feb. 11, 2016

Related U.S. Application Data

(60) Provisional application No. 61/782,251, filed on Mar. 14, 2013.

(30) Foreign Application Priority Data

Mar. 14, 2013 (GB) .................................. 1304577.8

(51) Int. Cl.
A61M 5/315 (2006.01)
A61M 5/24 (2006.01)
A61M 5/31 (2006.01)

(52) U.S. Cl.
CPC ...... *A61M 5/31536* (2013.01); *A61M 5/3156* (2013.01); *A61M 5/3158* (2013.01);
(Continued)

(58) Field of Classification Search
CPC .......... A61M 5/31536; A61M 5/31555; A61M 5/3156; A61M 5/3158; A61M 5/31595;
(Continued)

(56) References Cited

U.S. PATENT DOCUMENTS

| | | |
|---|---|---|
| 5,921,966 A | 7/1999 | Bendek et al. |
| 5,957,896 A | 9/1999 | Bendek et al. |

(Continued)

FOREIGN PATENT DOCUMENTS

| | | |
|---|---|---|
| EP | 0 897 728 | 2/1999 |
| EP | 1 923 083 | 5/2008 |

(Continued)

OTHER PUBLICATIONS

Notice of Reasons for Rejection for Japanese Patent Application No. 2015-562208; dated Nov. 7, 2016.

*Primary Examiner* — Emily L Schmidt
*Assistant Examiner* — Alexandra Lalonde
(74) *Attorney, Agent, or Firm* — Baker & Hostetler LLP

(57) ABSTRACT

A dispensing mechanism for administering a dosage of a medicament includes dosage setting means (7) for setting the dosage of a medicament to be administered; expelling means (15) for expelling a medicament from a medicament container; and coupling means (21) operatively coupled with the dosage setting means (7) and the expelling means (15), wherein the coupling means (21) is arranged to convert displacement of the dosage setting means (7) into a displacement of the expelling means (15) in a first direction, wherein the expelling means (15) includes a ratchet means (18a, 18b), and wherein the mechanism includes a first and (Continued)

a second independently moveable resisting pawl (14a, 14b) means facing a common side of the ratchet means (18), the first and the second resisting pawl means (14a, 14b) being configured to engage with the ratchet means (18a, 18b) and resist displacement of the expelling means (15) in a second direction opposite to said first direction.

19 Claims, 15 Drawing Sheets

(52) U.S. Cl.
CPC .... *A61M 5/31555* (2013.01); *A61M 5/31575* (2013.01); *A61M 5/31585* (2013.01); *A61M 5/31595* (2013.01); *A61M 5/24* (2013.01); *A61M 5/31556* (2013.01); *A61M 2005/2411* (2013.01); *A61M 2005/3126* (2013.01)

(58) Field of Classification Search
CPC .......... A61M 5/31575; A61M 5/31533; A61M 5/31563; A61M 2005/3125; A61M 2005/3126; A61M 5/24; A61M 5/178; A61M 5/31578; A61M 5/1407; A61M 5/1408; A61M 5/1422; A61M 5/16827
See application file for complete search history.

(56) References Cited

U.S. PATENT DOCUMENTS

| | | | | |
|---|---|---|---|---|
| 5,997,511 | A * | 12/1999 | Curie | A61M 5/315 604/110 |
| 2006/0069355 | A1 * | 3/2006 | Judson | A61M 5/31511 604/211 |
| 2012/0010575 | A1 * | 1/2012 | Jones | A61M 5/31555 604/211 |
| 2012/0271243 | A1 * | 10/2012 | Plumptre | A61M 5/3146 604/189 |
| 2012/0289929 | A1 * | 11/2012 | Boyd | A61M 5/31555 604/506 |
| 2013/0006193 | A1 * | 1/2013 | Veasey | A61M 5/31543 604/211 |
| 2013/0184653 | A1 * | 7/2013 | Moller | A61M 5/31525 604/211 |
| 2013/0338601 | A1 * | 12/2013 | Cowe | A61M 5/2033 604/189 |

FOREIGN PATENT DOCUMENTS

| | | | | |
|---|---|---|---|---|
| WO | WO 2003/057285 | | 7/2003 | |
| WO | WO 2004/035113 | | 4/2004 | |
| WO | WO 2008/148864 | | 12/2008 | |
| WO | WO 2011060785 | A1 * | 5/2011 | ........ A61M 5/31551 |

* cited by examiner

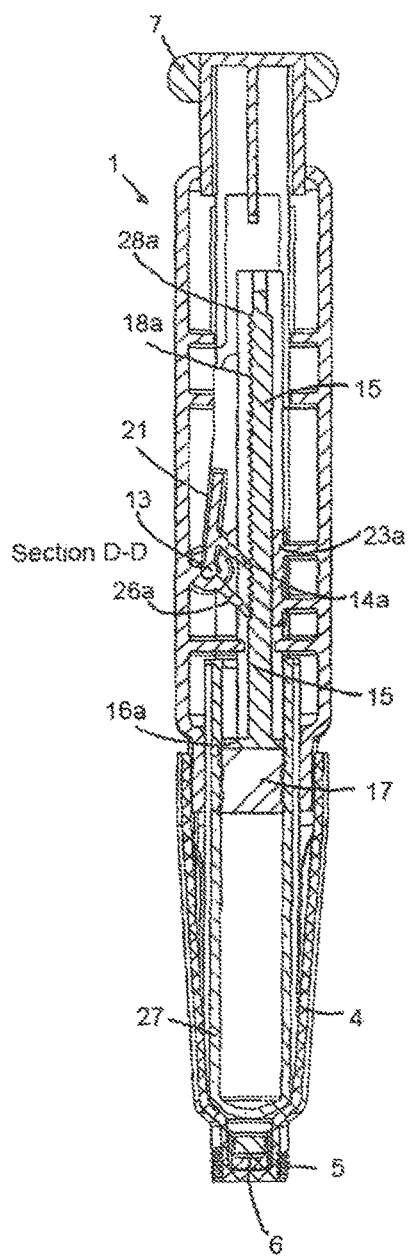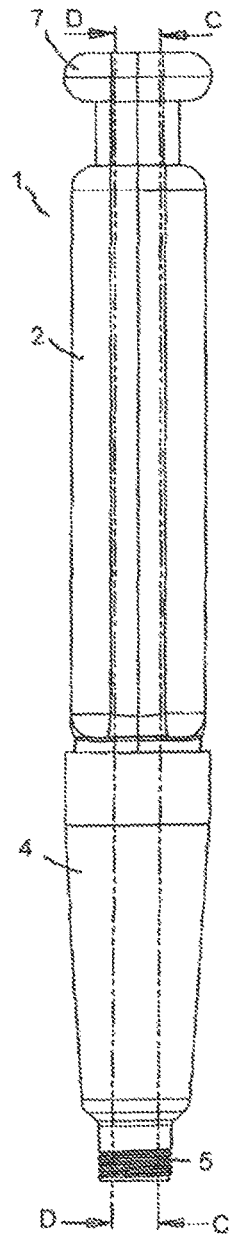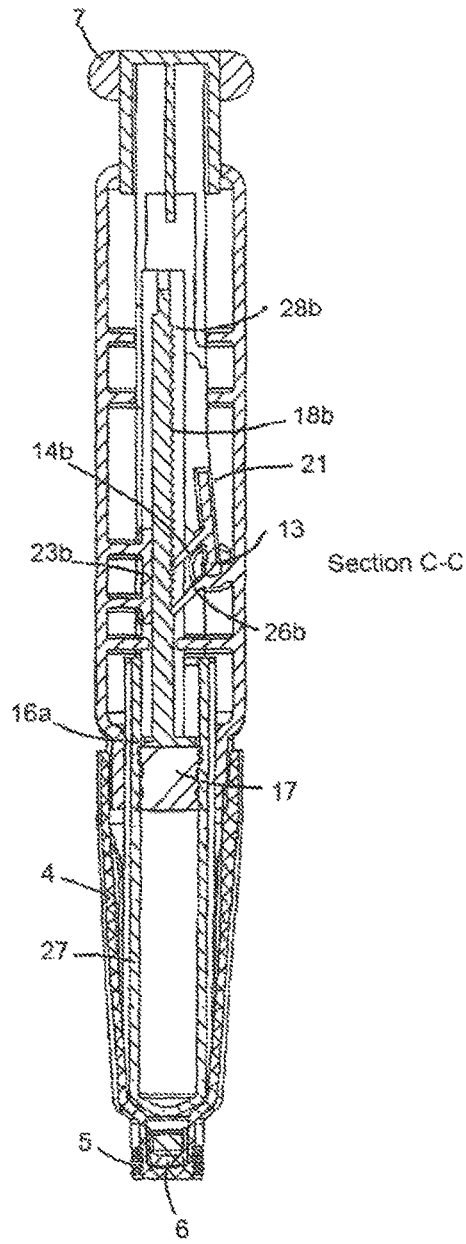

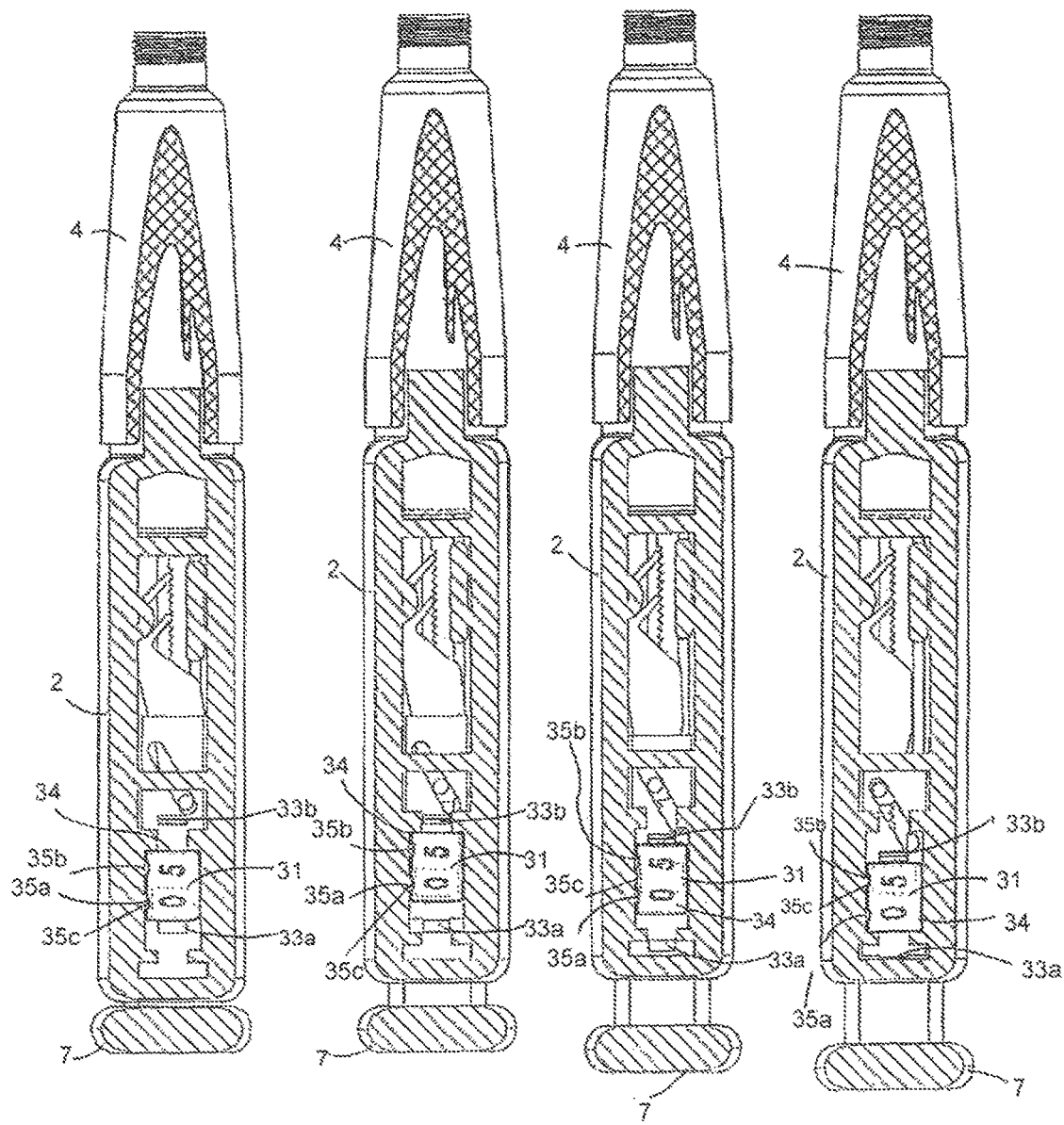

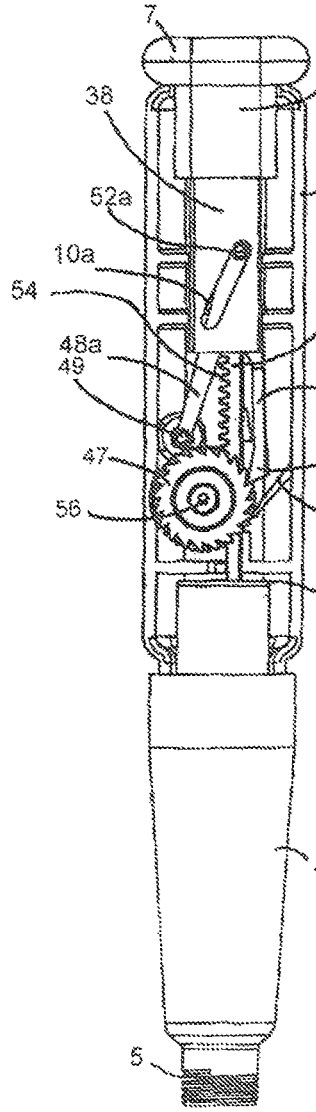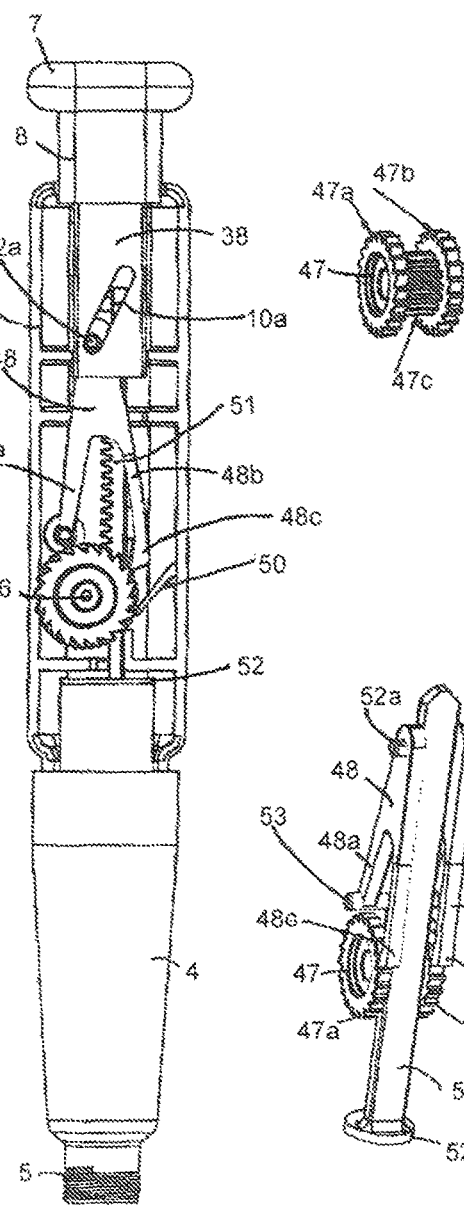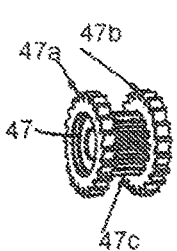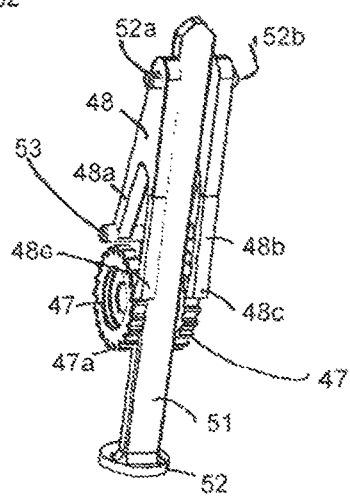

DISPENSING MECHANISM FOR A MEDICAL DEVICE

CROSS-REFERENCE TO RELATED APPLICATIONS

This application is the National Stage of International Application No. PCT/EP2014/055130, filed Mar. 14, 2014, which claims the benefit of Great Britain application number 1304577.8, filed Mar. 14, 2013 and U.S. provisional application number 61/782,251, filed Mar. 14, 2013, the disclosures of which are incorporated herein by reference in their entireties.

The present invention relates to a dispensing mechanism for administering a dosage of a medicament. The present invention also relates to a medical device comprising a dispensing mechanism, an injection device comprising a dispensing mechanism and an inhaler comprising a dispensing mechanism.

Medical devices for administering medicament are known, for example liquid solutions or powders can be delivered to a user or patient using injection devices or powder inhalers respectively.

One such medical device for administering a liquid solution is an injection device comprising a dispensing mechanism in which the dosage to be administered may be set by a dosage button moveable by a user or patient. A subsequent further movement of the dosage button, typically in the proximal direction of the device, i.e. in a direction towards an injection site of the device on the patient's skin, serves to inject the medicament using a ram to displace a plunger in a vial or cartridge of liquid medicament. A needle is typically attached to the cartridge in order to allow a subcutaneous delivery of the medicament. The dispensing mechanism ensures that a controlled and accurate dose may be administered.

However, such drive mechanisms often include several interacting component parts and thus packaging the components within a medical device that is optimal in size to carry and simplicity to use can be difficult. In addition, it cannot always be readily determined by a user of the device whether the correct dosage has been fully administered.

The present invention aims to alleviate at least to a certain extent at least one of the problems of the prior art.

According to a first aspect of the invention, there is provided a dispensing mechanism for administering a dosage of a medicament, the mechanism comprising: a dosage setting means, element, part or parts for setting a dose of medicament to be administered; expelling means, element part of parts for expelling a medicament from a medicament container; a coupling means, element, part of parts operatively coupled with the dosage setting means and the expelling means, wherein the coupling means is arranged to convert displacement of the dosage setting means into a displacement of the expelling means in a first direction, wherein the expelling means or coupling means includes a ratchet means, element, part or parts, and wherein the mechanism includes a first and a second independently moveable resisting pawl means or pawls facing a common side of the ratchet means, the first and the second resisting pawl means being configured to engage with the ratchet means and resist displacement of the expelling means in a second direction opposite to said first direction.

Advantageously, such a mechanism provides a compact arrangement and control of the expelling means. The resisting pawl means advantageously prevents movement of the expelling means during dose setting.

The dosage setting means may comprise a push button or other component which can be manually manipulated by a user.

Optionally, the ratchet means comprises a first and a second set of teeth, the first set of teeth being arranged to engage with the first resisting pawl means and the second set of teeth being arranged to engage with the second resisting pawl means.

The first and second sets of teeth are optionally each arranged in rows. The rows are optionally parallel and may be spaced from one another. The teeth preferably comprise peaks and valleys. The ridges of the peaks of each set of teeth are aligned transverse to the longitudinal axis of the expelling means. The teeth are preferably equally spaced in each row of teeth. The heights of the teeth are preferably equal.

Each tooth preferably comprises a front planar face and a rear planar face. The front planar face is preferably arranged proximally, i.e. nearer the point of contact with a patient's skin, in use, in the mechanism. The front face is preferably inclined at a smaller angle to a plane extending parallel to a side of the body of the mechanism or device and the rear face of each tooth being inclined at a relatively larger angle to said plane.

The engaging faces are preferably the faces of the teeth against which the pawls may act to resist movement. The engaging faces are preferably the rear faces of the teeth in each row of teeth.

The pawls may be orientated with their free, ratchet-engaging ends angled towards a first, proximal end of the mechanism.

Optionally, the dosage setting means is linearly displaceable in a direction substantially parallel to the longitudinal axis of the expelling means.

Optionally, the dosage setting means is rotationally displaceable about an axis substantially parallel to the longitudinal axis of the expelling means.

Optionally, the dosage setting means is displaceable both axially and rotationally about an axis parallel to the longitudinal axis of the expelling means, for example where a screw thread arrangement is provided.

Optionally, the first and/or second resisting pawl means comprise(s) or are formed with a part of a body of the mechanism.

Optionally, the mechanism may be formed of a plastics material, a metallic material or a combination of both.

Optionally, the teeth pitch in each of the first set of teeth and the second set of teeth is substantially equal.

Optionally, engaging faces of the second set of teeth are arranged offset from engaging faces of the first set of teeth on the ratchet means. Preferably, the offset is in the longitudinal direction of the expelling means.

Optionally, the engaging faces of the teeth in the first set of teeth are offset a distance of half the tooth pitch, i.e. half the distance between adjacent engaging faces from the teeth of the second set of teeth. Preferably, the offset is in the longitudinal direction of the expelling means.

Optionally, the resisting pawls are offset in the longitudinal direction of the expelling means. Optionally, the ratchet comprises a single set of teeth engageable with the resisting pawls. This allows for an alternative arrangement in order to achieve fine dosages. Optionally, the offset of the resisting pawls may be, for example, 0.5 or 1.5 times the pitch or distance between adjacent teeth in the ratchet.

Advantageously, by arranging the teeth or pawls so that only one pawl engages with an engaging face of one of the two sets of teeth at any one time, finer doses can be dispensed whilst the component features remain the same size.

Optionally, the expelling means comprises a longitudinal member.

Optionally, the expelling means is formed with ribs, or protrusions to be received in or be guided in corresponding recesses or channels. This ensures smooth motion of the expelling means.

Optionally, the first and second resisting pawl means are formed on opposing parts of a body of the mechanism. This reduces the number of components and can provide strength to the resisting pawls.

Optionally, the body may be formed of two half-shells.

A dispensing mechanism is also provided, wherein the first and the second resisting pawl means are aligned in a substantially common plane. Alternatively, the first and the second resisting pawls means could be aligned offset with the teeth in the ratchet being in alignment.

Optionally, the first resisting pawl means is aligned adjacent the second resisting pawl means.

Optionally, the coupling means comprises a drive means or driver comprising a pair of drive pawls engageable in said ratchet means for displacing said expelling means.

Optionally, the drive pawls are arranged in adjacent alignment or may be offset corresponding to the offset of the resisting pawls.

Optionally, the coupling includes a guide slot in which a follower on the drive means is received and configured such that the drive means is moved as a result of movement of the dosage setting means. Optionally, the driver is caused to rotate about a pivot in order to engage the drive pawls with the teeth in the ratchet and produce motion of the expelling means.

Alternative coupling means may include gears or thread arrangements in order to produce a displacement of the expelling means upon movement of the dosage means.

Optionally, the expelling means comprises a ram means.

According to a second aspect of the invention, there is provided a dispensing mechanism for administering a dosage of a medicament, the mechanism comprising: a body; and dosage setting means, element, part of parts for setting the dosage of a medicament to be administered, the dosage setting means being moveable in a first direction for setting the dose and in a second direction for administering the dose, wherein the mechanism further comprises an indication element, the indication element being arranged to be displaced by a predetermined movement of the dosage setting means; and wherein the indication element is arranged such that the indication element remains unmoved relative to said body of the mechanism during at least part of said movement of the dosage setting means.

In this way, the indication element can provide a static indication to a user for at least part of the motion of the dosage setting means. This can serve to facilitate operation of the mechanism or device by a user.

Optionally, the indication element is movable within a guide channel. Advantageously, this maintains the orientation of the indication element.

Optionally, the indication element is slidingly supported in or on the body.

Optionally, the dosage setting means is movable in an axial direction substantially parallel to the longitudinal axis of the body.

Optionally, the indication element is formed as a planar element, preferably as a generally rectangular plate or element.

Optionally, the dosage setting means is rotatable about the longitudinal axis of the body.

Optionally, the dosage setting means is operative coupled to a first and a second engagement means, elements or parts, the first engagement means and the second engagement means being engageable with the indication element such that upon engagement, movement of the dosage setting means causes displacement of the indication element.

The engagement means are preferably formed to engage with the indication element in order to move it with corresponding movement of the dosage setting means.

Optionally, the engagement elements are arranged spaced from one another at a distance greater than a length of the indication element. This then provides a degree of lost motion of the indication element relative to the dosage setting element.

Optionally, resisting means, elements or parts are provided, the resisting means being arranged to resist movement of the indication element relative to movement of the dosage setting means. This prevents movement of the indication element until a predetermined movement of the dosage setting means has been made.

Optionally, the resisting means comprises a protrusion receivable in a corresponding recess. The protrusion may be provided on the body or dosage setting element or on the indication element or vice versa, for example. This provides a degree of mechanical resistance without additional parts.

Optionally, the resisting means comprises a protrusion receivable in a corresponding recess.

Optionally, the mechanism includes an aperture through which at least a portion of the indication element is exposed, in use, to a user.

Optionally, the indication element comprises tactile and/or visual indications. This may include Braille or other types of tactile indications and/or visual indications such as lights or printed numbers. The indications may indicate the state of the mechanism or device, e.g. whether a dose is ready to be administered or if a dose needs to be set.

Optionally, the indication element is moved directly by the dosage setting means. The indication element may be in direct contact with the dosage setting means.

Optionally, the indication element is moved indirectly by the dosage setting means.

According to a third aspect of the invention, there is provided a dispensing mechanism for administering a dosage of a medicament, the mechanism comprising: a body; dosage setting means, element, part or parts for setting the dosage of a medicament to be administered, the dosage setting means being moveable in a first direction for setting the dose and in a second direction for administering the dose; and an indication element, the indication element being arranged to be displaced by a predetermined movement of the dosage setting means; and wherein the mechanism further includes conversion means, element, part of parts configured, during displacement of the indication element, to convert a movement of the dosage setting means of a first magnitude into a movement of the indication element of a second magnitude, and wherein said first magnitude of movement is different to said second magnitude of movement.

In this way, the degree of movement of the indication element can be configured to be different in magnitude to that of the dosage setting means.

Optionally, the first magnitude of movement is greater than the second magnitude of movement. In this way, a small movement of the dosage setting means can cause a larger movement of the indication element.

Optionally, the first magnitude of movement is smaller than the second magnitude of movement. As such, the indication element can be arranged to move a shorter distance that the movement of the dosage setting means.

Optionally, the conversion means is configured to move the indication element during all movement of the dosage setting means. The conversion means may be in constant contact with the dosage setting means or in constantly coupled thereto, for example through an intermediate component.

Optionally, the indication element remains unmoved relative to the body of the mechanism during at least part of said movement of the dosage setting means.

Optionally, the indication element is movable within a guide channel.

Optionally, the indication element is slidingly supported in or on the body.

Optionally, the dosage setting means is movable in an axial direction substantially parallel to the longitudinal axis of the body.

Optionally, the dosage setting means is rotatable about the longitudinal axis of the body.

Optionally, the conversion means comprises a first and a second engagement means operatively coupled to the dosage setting means, the first engagement means and the second engagement means being engageable with the indication element such that upon engagement, movement of the dosage setting means causes displacement of the indication element.

Optionally, the engagement elements are arranged spaced from one another at a distance greater than a length of the indication element.

Optionally, the conversion means comprises a lever.

Optionally, the lever acts about a fulcrum operatively coupled to the dosage setting means. The relative magnitudes of movement of the dosage setting means and indication element may be configured by the relative lengths of the lever either side of the fulcrum.

Optionally, the lever is reliantly flexible. In this way dimensional tolerances may be accounted for as the lever may flex if movement of the dosage setting means is greater that the space in which the lever is located.

Optionally, the lever is pivotally attached to said body.

Optionally, the lever is formed integrally with said body. This can serve to reduce manufacturing costs and reduce the number of parts in the mechanism. The lever could alternatively be any part of the body, indicator or dose setting means, for example.

Optionally, resisting means are provided, the resisting means being arranged to resist movement of the indication element relative to movement of the dosage setting means.

Optionally, the resisting means comprises a protrusion receivable in a corresponding recess.

Optionally, the mechanism includes an aperture through which at least a portion of the indication element is exposed, in use, to a user.

Optionally, the indication element comprises tactile and/or visual indications.

Optionally, the indication element is moved directly by the dosage setting means.

Optionally, the indication element is moved indirectly by the dosage setting means.

According to a fourth aspect of the invention, there is provided a dispensing mechanism for administering a dosage of a medicament, the mechanism comprising: a dosage setting means, element, part or parts for setting a dose of medicament to be administered; expelling means, element, part of parts for expelling a medicament from a medicament container; a coupling means, element, part or parts operatively coupled with the dosage setting means and the expelling means, wherein the coupling means is arranged to convert displacement of the dosage setting means into a displacement of the expelling means in a first direction, wherein the coupling means includes a ratchet means, element or part or parts comprises a first and a second ratchet wheels, and wherein the mechanism includes a first and a second independently moveable resisting pawl means facing the ratchet means, the first and the second resisting pawl means being configured to engage with the first and second ratchet wheels respectively and resist displacement of the expelling means in a second direction opposite to said first direction.

Advantageously, such a mechanism provides a compact arrangement and control of the expelling means. The resisting pawl means advantageously prevents movement of the expelling means during dose setting.

Optionally, the first ratchet wheel comprises a first set of teeth and the second ratchet wheel comprises a second set of teeth, the first set of teeth being arranged to engage with the first resisting pawl means and the second set of teeth being arranged to engage with the second resisting pawl means.

Optionally, engaging faces of the second set of teeth are arranged rotationally offset from engaging faces of the first set of teeth on the ratchet means. Each of the first and second ratchet wheels may have teeth provided around their entire circumference. The first and second ratchet wheels preferably share a common rotational axis.

Optionally, the dosage setting means is linearly displaceable in a direction substantially parallel to the longitudinal axis of the expelling means.

Optionally, the dosage setting means is rotationally displaceable about an axis substantially parallel to the longitudinal axis of the expelling means.

Optionally, the first and/or second resisting pawl means comprise(s) a part of a body of the mechanism.

Optionally, the angular teeth pitch in each of the first set of teeth and the second set of teeth is substantially equal.

Optionally, the engaging faces of the teeth in the first set of teeth are offset by an angle of rotation of half the angle of rotation between adjacent engaging faces from the teeth of the second set of teeth.

Optionally, the expelling means comprises a longitudinal member.

Optionally, the first and second resisting pawl means are formed on opposing parts of a body of the mechanism.

Optionally, the first and the second resisting pawl means are aligned in a substantially common plane.

Optionally, the first resisting pawl means is aligned adjacent the second resisting pawl means.

Optionally, the coupling means comprises a drive means comprising a pair of drive pawls engageable in said ratchet means for rotation of said ratchet wheel. The drive pawls may be spaced from one another to align either side of the expelling means.

Optionally, the drive pawls are arranged in adjacent alignment.

Optionally, the coupling includes a guide slot in which a follower on the drive means is received and configured such that the drive means is moved as a result of movement of the dosage setting means.

Optionally, the ratchet means comprises a gear wheel engageable with a corresponding set of teeth on the expelling means. The gear wheel preferably shares a common axis of rotation with the ratchet wheels. The teeth on the expelling means are preferably formed as a rack of teeth. The rotation of the gear wheel preferably results in axial movement of the expelling means.

Optionally, the first and second ratchet wheels are arranged either side of said gear wheel.

Optionally, the diameter of the gear wheel is smaller than the diameter of each of the ratchet wheels. The ratchet wheels may be aligned either side of the expelling means. The gear wheel and ratchet wheel may be formed integrally as a single piece.

Optionally, the expelling means comprises a ram means.

Any one or more of the first to fourth aspects of the invention or any optional feature thereof may be combined. Advantages of the features are applicable to different aspects and embodiments of the invention.

According to a fifth aspect of the invention, there is provided a medical device comprising a dispensing mechanism according to any of the first to fourth aspects of the invention and any optional feature thereof.

Optionally, the medical device may comprise a medicament container such glass vial, cartridge or foil pack and/or a receiving part for such a medicament container.

According to a sixth aspect of the invention, there is provided an injection device comprising a dispensing mechanism according to any of the first to fourth aspects of the invention and any optional feature thereof.

According to a seventh aspect of the invention, there is provided an inhaler comprising a dispensing mechanism according to any of the first to fourth aspects of the invention and any optional feature thereof.

The present invention will now be described by way of an examplary embodiment, with reference to the accompanying drawings, in which:

FIGS. 15 and 17 show cross-sections C-C and D-D respectively of the medical device as marked in FIG. 16 with the dosage button in a withdrawn state;

FIG. 18b shows a detail view A as circled in the ratchet view shown in FIG. 18a;

FIG. 19a shows a plan view along the length of the ratchet as shown in FIG. 18a;

FIG. 19b shows a detail view B as circled in the ratchet view as shown in FIG. 19a;

FIG. 20 shows a perspective view of the ratchet as shown in FIG. 18a;

FIG. 25 shows a cross-sectional view E-E of FIG. 21 showing the dosage button in an initial depressed state;

FIG. 26 shows a cross-section view E-E of FIG. 21 showing the dosage button in an initial retracted state;

FIG. 27 shows a cross-section view E-E of FIG. 21 showing the dosage button in an intermediate retracted state;

FIG. 28 shows a cross-section view E-E of FIG. 21 showing the dosage button in an fully retracted state;

FIG. 40 shows a view of a further medical device comprising an alternative dispensing mechanism with part of the body removed with a push button in a depressed state;

FIG. 41 shows a further view the medical device of FIG. 40 with the push button in a retracted state;

FIG. 42 shows a view of the coupling means and expelling means of the dispensing mechanism shown in FIGS. and 41; and FIG. 43 shows a view of a rotary ratchet of the expelling means of the dispensing mechanism of FIG. 42.

Figures 1, 2:
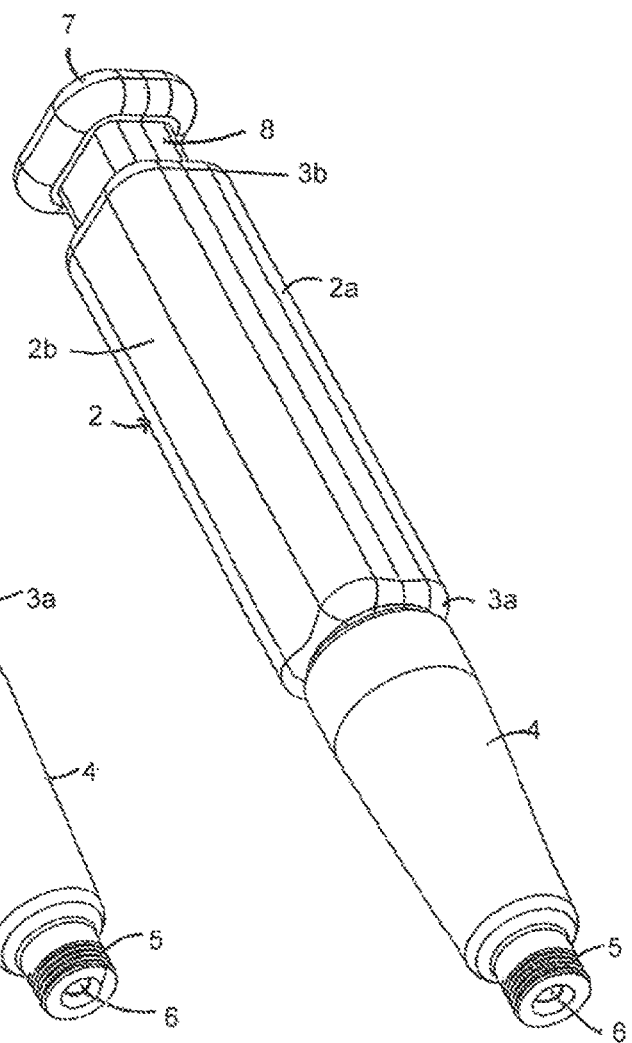
FIG. 1 shows a perspective view of a medical device with a dispensing mechanism comprising a dosage button in a depressed state.
FIG. 2 shows a perspective view of the medical device of FIG. 1 with a dosage button in a withdrawn state.

FIG. 1 shows a perspective view of a medical device including a dispensing mechanism generally indicated 1. The medical device 1 comprises an elongate body 2 with a substantially square cross-section with rounded edges between adjacent sides. However, it is envisaged that the body 2 may be formed in any suitable shape, for example with a circular cross-section or with varying cross section along the length of the device 1.

The size and the form of the body 2 may be designed to facilitate being held in a user or patient's hand. The surface may be provided with surface protrusions or knurling or any other such surface texture to facilitate gripping of the device 1.

At a first, proximal end 3a of the body 2, i.e. the end nearest an injection site of a user in use, a cartridge receptacle 4 is attached, for example by a bonded or clipped engagement, to the body 2, for holding a medicament cartridge or carpule. The cartridge receptacle 4 is formed generally as a truncated cone and may be made transparent in order that a user may inspect the contents of the medicament cartridge to obtain a visual indication of the quantity of medicament remaining. The medicament cartridge may be filled with a liquid medicament, for example insulin.

A removable and disposable needle (not shown) may be attached to the cartridge receptacle 4 or to a threaded engagement 5 provided on the outer surface of a cylindrical part at the proximal end of the cartridge which, as shown in FIG. 1, extends through the end of the cartridge receptacle 4. A typical needle comprises a rear needle part for puncturing a plastic stopper 6 provided at the proximal end of the medicament cartridge. The needle also comprises a forward needle part. In use, the forward needle part may be inserted subcutaneously into a patient so that medicament may be injected from the medicament cartridge into a patient.

At a second, distal end 3b of the body 2 of device 1, i.e. the end, in use, furthest from an injection site of a user, a dosage setting means or element is provided in the form of a push button 7. In the embodiment, the push button has a similar, generally square, cross-sectional shape to that of the body 2 of the device 1. However, different shapes and arrangements of the dosage means are envisaged. The dosage means 7 is typically sized to be gripped between a finger and thumb of a user. FIG. 1 shows the push button 7 in a depressed, i.e. pushed-in state relative to the body 2 of the device 1.

The push button 7 may be pulled out away from the body 2 in a first distal direction in order to set a dose and pushed in towards the body 2 in a second proximal direction in order to administer a dose of medicament.

In FIG. 2, the push button is shown in a first, pulled-out state, with the device ready to deliver a dose. The push button 7 comprises a drive shaft 8 connecting the push button to a drive mechanism within the body of the device.

The body 2, in the embodiment, is formed of two half-shells 2a, 2b. The body 2 is generally formed of a plastics material, which may be injection moulded or produced by any other suitable manufacturing technique.

Figure 3:
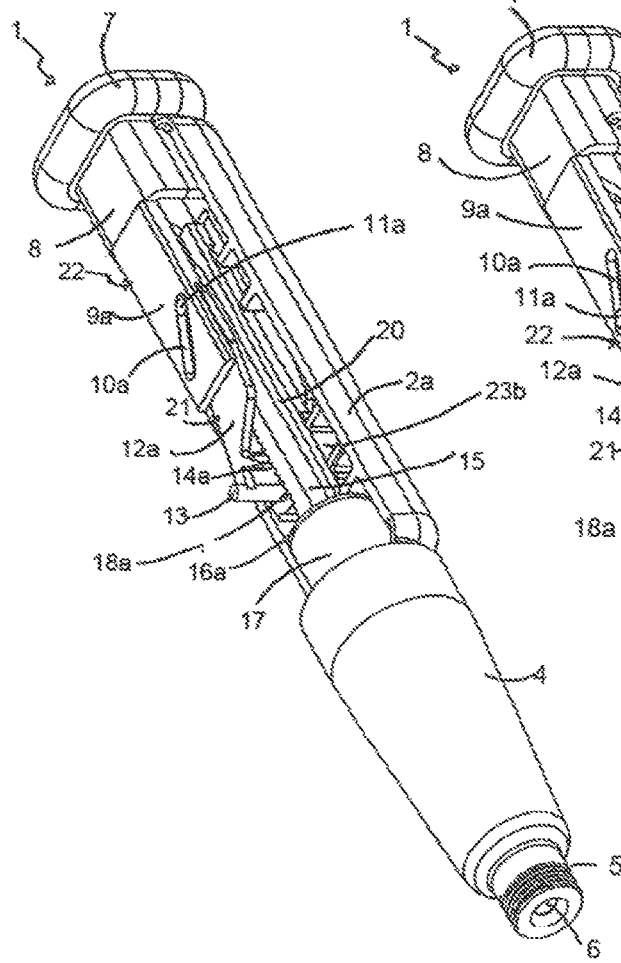
FIG. 3 shows a first side perspective view of the medical device of FIG. 1 with part of the outer body removed with the dosage button in a depressed state.

FIG. 3 shows the device 1 with one of the half-shells 2b removed to expose the internal drive mechanism of the device 1.

Within the body 2 of the device 1, an expelling means, element or part is provided in the form of a longitudinal drive rod 15. The rod 15 is linear in form and serves as a ratchet or ratchet means, with an upper surface comprising two sets of ratchet teeth 18a, 18b extending along at least part of the length of the rod 15. The teeth are orientated such that their lands, valleys or ridges of the peaks run transverse to the longitudinal direction of the device.

In the exemplary embodiment described herein, the teeth of one of the sets of ratchet teeth are offset from the teeth of the other set of ratchet teeth. However, it should be noted that such an 'offset' arrangement is only a preferred embodiment of the present invention.

The sets of ratchet teeth in this example are separated by a longitudinal planar divider 24. The longitudinal rear side of the rod 15 is planar with a central protruding guide rib 20. Corresponding channels and support rails 23a, 23b are formed within the body 2 to receive the rod 15 and the guide rib 20 and allow linear movement thereof along the longitudinal axis of the device 1.

At the proximal end of the rod 15, the rod comprises an engagement ram 16a in the form of a circular disc. The ram 16a is formed and sized such that, in use, the ram 16a can engage with and displace a plunger 17 in a medicament cartridge received in the cartridge receptacle 4.

A coupling means, element, part or mechanism is provided to couple the dosage setting element with the expelling element. In the embodiment, the coupling means includes a first coupling element 22 connected to the push button 5 via a shaft 8. In the embodiment, the first coupling element 22 is formed integrally with the shaft 8. However, it is envisaged that the coupling element 22 could be operatively coupled to the push button 7 and/or shaft via a sprung or biased coupling so as to be moveable relative thereto.

The coupling element 22 comprises a pair of spaced planar sections of which only the upper planar section 9a is visible in FIG. 3. However, a corresponding lower planar section is formed with the lower side of the shaft of the push button 7. The spaced planar sections 9a are perpendicular to the plane of the surface on which the ratchet teeth are provided. In the upper planar section 9a of the coupling element 22, a diagonal slot 10a is provided. The diagonal slot 10a extends diagonally in a direction across the body of the device.

Figure 4:
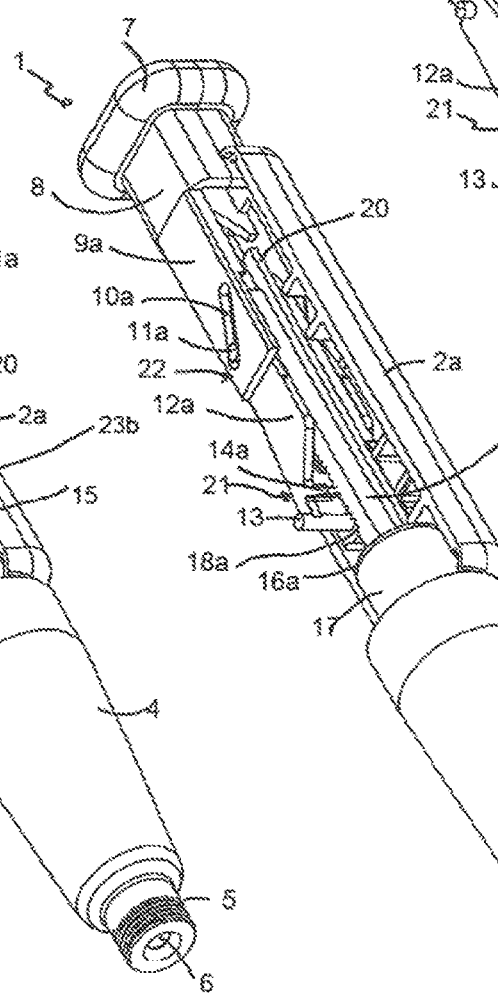
FIG. 4 shows a first side perspective view of the medical device of FIG. 1 with part of the outer body removed with the dosage button in a withdrawn state.
Figure 5:
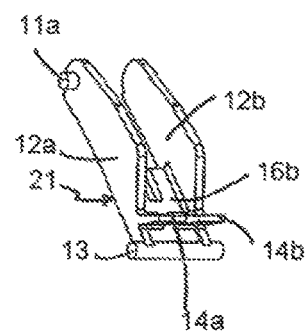
FIG. 5 shows a first side perspective view of a drive pawl of the medical device of FIG. 1.

The coupling further comprises a drive means or driver 21 which, as shown more clearly in FIG. 5, comprises a pair of parallel and spaced planar arms 12a, 12b connected via a transverse web 16b towards a proximal end thereof. Each of the planar arms 12a, 12b comprises a circular protrusion or follower of which only the upper protrusion 11a is visible in FIGS. 3 to 4.

The circular protrusion 11a of the upper planar arm 12a is received in the diagonal guide slot 10a of the upper planar section 9a of the coupling element. Although not shown, a corresponding circular protrusion is formed on the lower planar arm 12b and is received in a corresponding diagonal guide slot 10a in the lower planar section of the coupling element 22.

The underside of the upper planar section 9a of the coupling element 22 is supported on and slides atop of the upper planar arm 12a of the driver 21.

The driver 21 comprises a pair of drive pawls 14a, 14b extending from the web 16b. A gap is provided between the drive pawls 14a, 14b which fits around the divider 24 between the two sets of ratchet teeth 18a, 18b. The drive pawls are independently flexible about their connection with the driver 21.

The driver 21 comprises a cylindrical portion 13a which is pivotally located in a corresponding hole in the body 2 of the device 1. The cylindrical portion is rotatably engaged with the hole in the body 2 such that the driver 21 may rotate about the axis of the cylindrical portion, which acts therefore as a pivot axis.

The drive pawls 14a, 14b are arranged such that they can engage with a tooth respectively of each of the sets of ratchet teeth 18, although due to the offset in the sets of teeth, the drive pawls 14a, 14b do not necessarily contact the same part of a tooth in a respective set of teeth. For example, with an offset arrangement of the two sets of teeth in the drive rod, one drive pawl may be in engagement with a rear face of a tooth and the other drive pawl may be atop a ridge or peak of a tooth in the adjacent set of teeth. The drive pawls 14a, 14b of the driver 21 are angled towards the proximal end 3a of the body 2 of device 1. However, embodiments are envisaged where the teeth in each set of teeth are in adjacent alignment.

FIG. 4 shows a further view of the device 1 as shown in FIG. 3 with the push button 7 in a retracted or withdrawn position.

As can been in FIGS. 3 and 4, in the depressed state of the push button 7, the engagement protrusion 11a of the driver 22 is located at one end, the distal end, of the diagonal slot 10a of the coupling element 22. In the withdrawn position of the push button 7, the engagement protrusion 11a of the driver 22 is located at the other end, the proximal end, of the diagonal slot 10a of the coupling element 22. This change of position is achieved by the engagement protrusion 11a sliding in the diagonal slot 11a as the push button 7 is moved in a direction along the longitudinal axis of the device.

Because of the diagonal orientation of the slot 11a in the coupling element, the movement of the engagement protrusion 11a, which is formed with the driver 21, causes the driver 21 to rotate about the pivot point formed by the engagement of the cylindrical protrusion 13 of the driver 21 engaged in the body 2 of the device 1.

As the driver 21 is rotated clockwise about the pivot axis 13 by the push button 7 being depressed, one of the pawls 14a, 14b engages with at least one rear face of a tooth on one of the sets of ratchet teeth 18a such that the longitudinal rod 15 is displaced in a direction towards the proximal end of the device.

Figures 6, 7, 8:
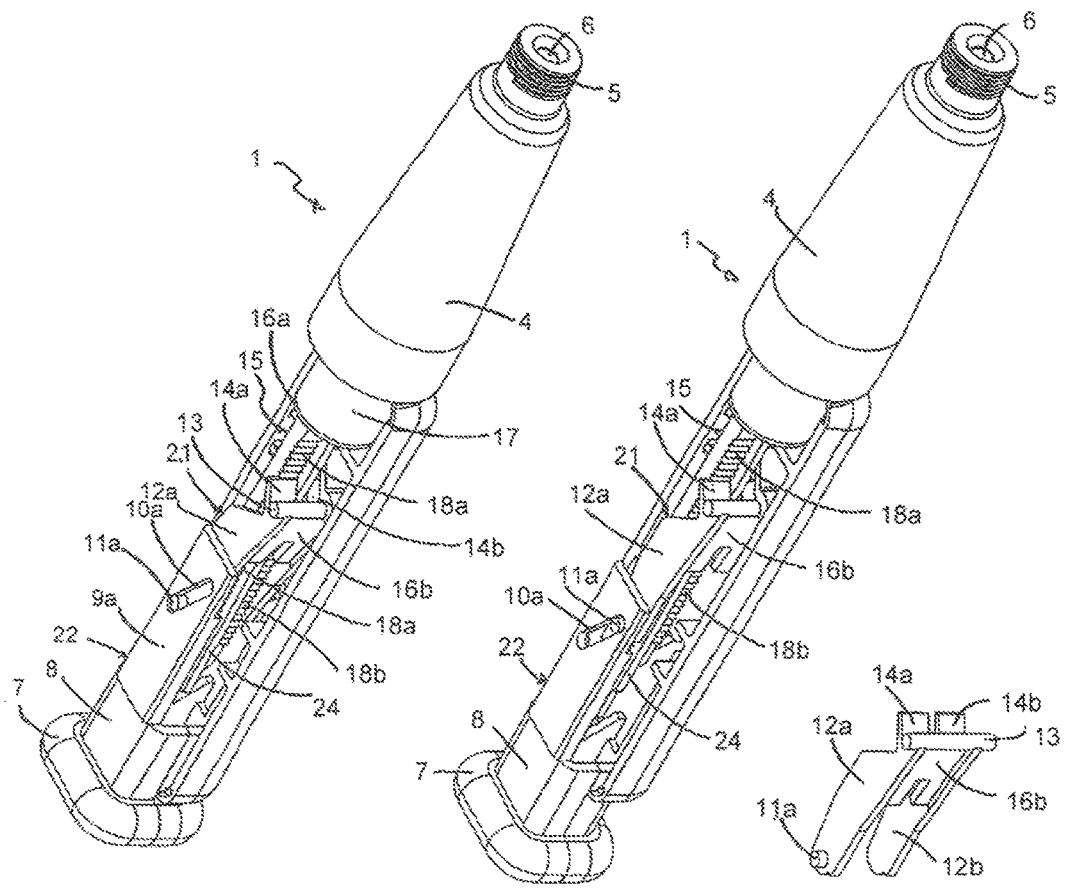
FIG. 6 shows a second side perspective view of the medical device of FIG. 1 with part of the outer body removed with the dosage button in a depressed state.
FIG. 7 shows a second side perspective view of the medical device of FIG. 1 with part of the outer body removed with the dosage button in a withdrawn state.
FIG. 8 shows a second side perspective view of a drive pawl of the medical device of FIG. 1.

FIGS. 6, 7 and 8 show reverse side perspective views respectively of the views shown in FIGS. 3, 4 and 5.

In FIG. 6, the device 1 is shown with the push button 7 in a depressed state. The longitudinal drive rod 15 can be seen showing the upper side thereof in which the two sets of ratchet teeth 18a, 18b are provided separated by divider 24. The upper and lower drive pawls 14a, 14b can be engaged with teeth respectively in the first and second sets of ratchet teeth 18a, 18b, although as described above, due to the offset of the teeth in the two sets of teeth 18a, 18b, the drive pawls 14a, 14b do not necessarily contact the same portion of a tooth in a respective set of teeth.

FIG. 7 shows the device 1 with the push button 7 in a withdrawn state. As can be seen from FIG. 6, with the push button 7 in a depressed state or position, the driver 21 has been rotated about the pivot axis 13 thus engaging at least one of the drive pawls 14a, 14b with at least one rear face of a tooth of a set of ratchet teeth 18a, 18b and causing the drive rod 15 to be displaced in a proximal direction.

The drive pawls 14a, 14b are formed to allow a degree of flexing relate to the web 16b.

Figure 9:
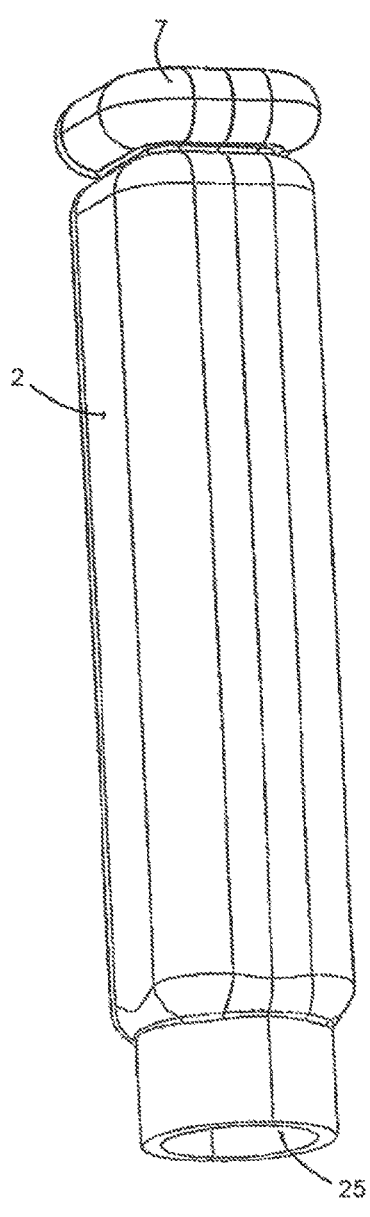
FIG. 9 shows a perspective side view of the medical device of FIG. 1 without a cartridge holder.

FIG. 9 shows a view of the device 1 with the push button 7 in a depressed state. The device 1 is shown with the cartridge receptacle 4 removed. An aperture 25 can be seen in the proximal end 3a of the body 2 in which the drive rod 15 may extend in use to engage with the stopper of a medicament cartridge (not shown).

Figure 10:
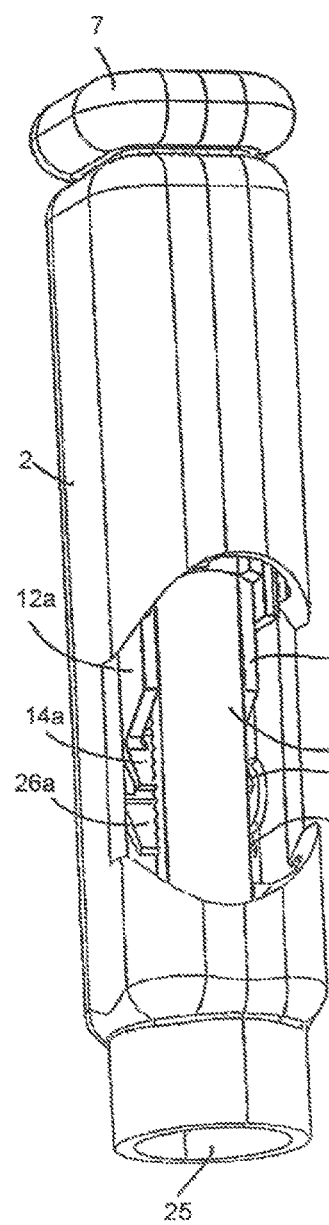
FIG. 10 shows a cutaway view through the body of the medical device as shown in FIG. 9 showing a rear view of a ratchet arrangement.

FIG. 10 shows a view of the device 1 with a cut-out in the body 2. Through the cut-out, the drive rod 15 may be seen. Either side of the drive rod 15, the upper and lower arms 12a, 12b of the driver are located. The upper and lower drive pawls 14a, 14b can also be seen.

Spaced from the upper and lower drive pawls 14a, 14b, in the proximal direction of the body 2 of the device 1, a pair of resistance or resisting pawls 26a, 26b is provided. The resistance pawls 26a, 26b are formed with or attached to the body 2 of the device 1.

Figure 11:
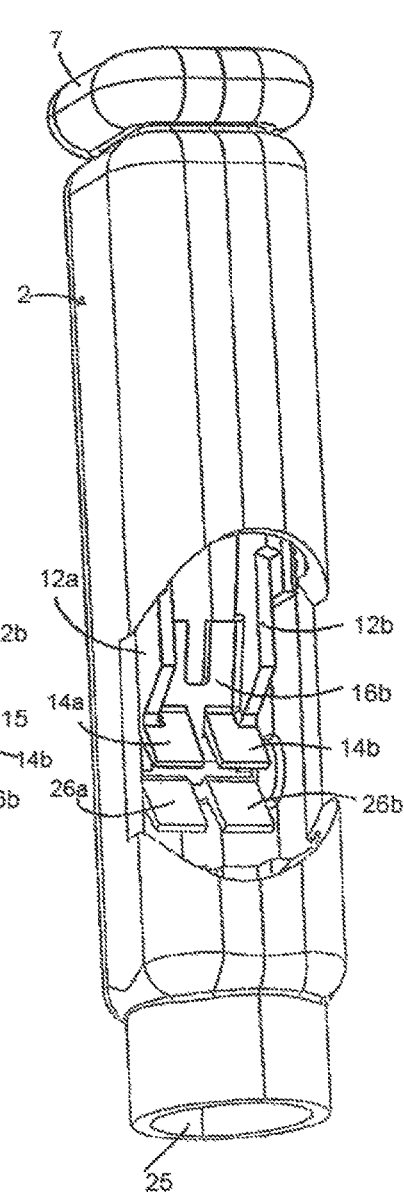
FIG. 11 shows a cutaway view through the body of the medical device as shown in FIG. 9, with the ratchet removed and showing the underside of the drive pawl.

FIG. 11 shows a further cut-away view of the body 2 of the device 1, but with the drive rod 15 removed. Here, the arrangement of the resistance pawls 26a, 26b and drive pawls 14a, 14b can be seen.

The resistance pawls 26a, 26b are angled in a direction towards the proximal end 3a of the body 2 of device 1. The resistance pawls are flexible to a certain degree with respect to the body 2 of the device 1.

The upper resistance pawl 26a can engage with the upper set of teeth 18a on the longitudinal rod 15, with the lower resistance pawl 26b engageable with the lower set of teeth 18b on the longitudinal rod 15. Due to the offset of the teeth between the teeth in one set of ratchet teeth to the teeth in the other set of ratchet teeth in this embodiment, the resistance pawls 26a, 26b may not contact the same part of a tooth in each of the first and second sets of ratchet teeth 18a, 18b.

The resistance pawls 26a, 26b serve to resist or prevent movement of the longitudinal rod 15 in a direction away from the proximal end 3a of the body 2 of device 1, by engaging the rear faces of the ratchet teeth 18a, 18b.

The operation of the device 1 will now be described with reference to FIGS. 12 and 14, which show cross sections A-A and B-B along the parallel longitudinal planes shown in FIG. 13.

Figures 12, 13, 14:
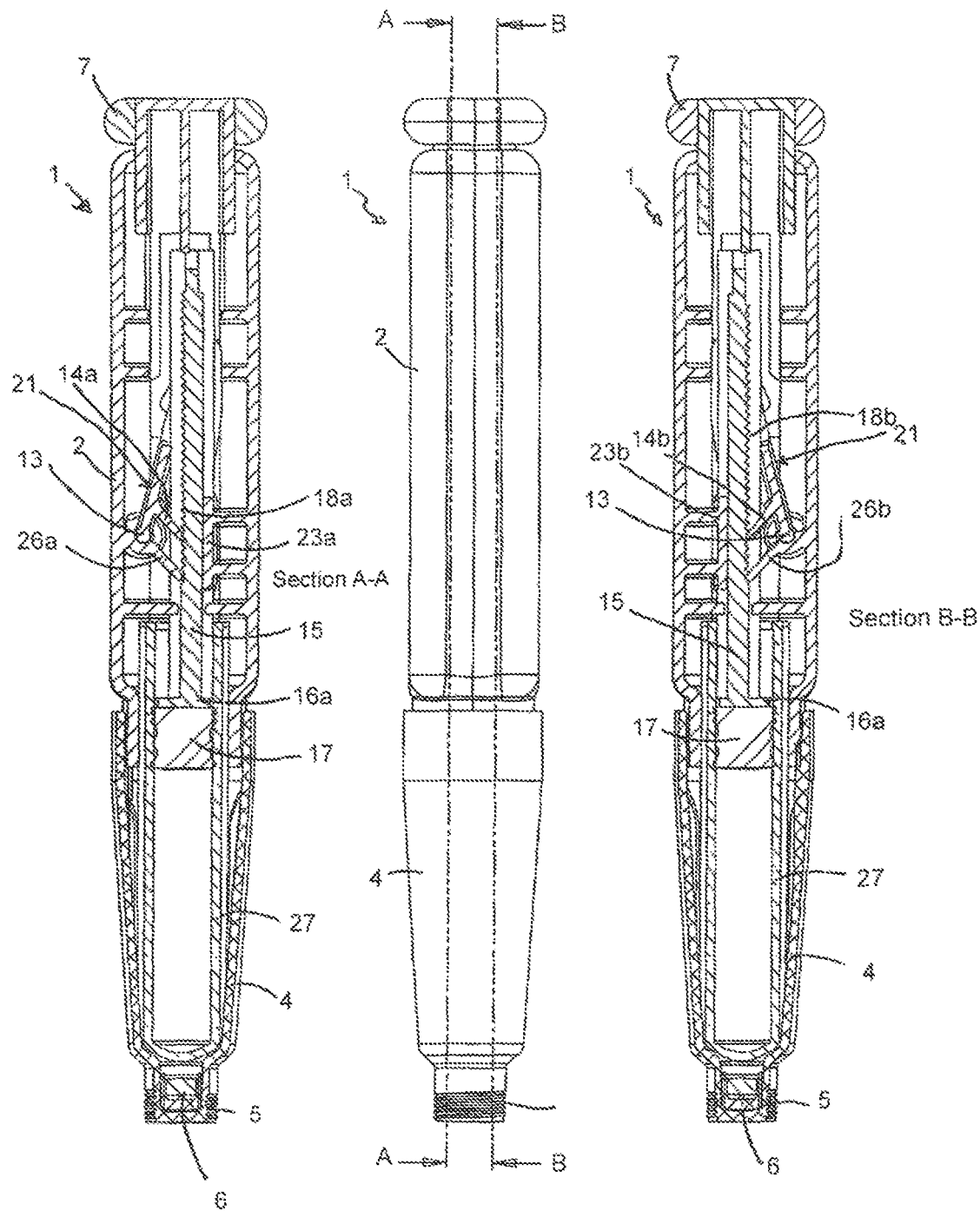
FIGS. 12 and 14 show cross-sections A-A and B-B respectively of the medical device as is marked in FIG. 13 with the dosage button in a depressed state.

FIGS. 12 and 14 show the device 1 with the push button 7 in a depressed state. A medicament cartridge 27 is shown within the cartridge receptacle 4. A plunger 17 is provided within the medicament cartridge 27 which can be moved by engagement and displacement of the ram 16a of the longitudinal or drive rod 15, which serves to expel the medicament from the cartridge 27. FIG. 14 is a lower side view of the device 1 and the description of the upper side as shown in FIG. 12 is equally applicable to the lower side.

The upper resistance pawl 26a and the distal edge thereof can be seen engaged with a rear face of a tooth of the upper set of ratchet teeth 18a on the longitudinal drive rod 15.

The upper drive pawl 14a can also be seen engaged with a rear face of a tooth of the upper set of ratchet teeth 18a on the longitudinal or drive rod 15.

In order to set a dose, a user must withdraw the push button 7 in a direction away from the cartridge receptacle 4, i.e. in a distal direction with respect to the body 2 of device 1.

As the push button 7 is withdrawn, as has been described in relation to FIGS. 3 to 8, the sliding or engagement protrusion 11a on the upper drive arm 12a of the driver, which is located in the diagonal slot 10a of the coupling element 22, slides in the slot, causing the driver 21 to rotate in an anti-clockwise direction about the pivot axis 13. During this movement, due to the offset of the sets of ratchet teeth 18a, 18b, one of the resistance pawls 26a, 26b acts to resist movement of the drive rod 15 in a distal direction by engagement with the rear face of the tooth.

As the driver 21 rotates, one of the drive pawls 14a, 14b slides from between a space or valley between two longitudinally adjacent peaks of two teeth, over the front tooth face and ridge of a tooth such that it proceeds to be located in the longitudinally adjacent space or valley between successive teeth. The other of the drive pawls also moves, but due to the offset in the sets of ratchet teeth 18a, 18b does not necessarily end up on the same part of a tooth. At this stage, the push button is then in a retracted state as shown in FIGS. 15 and 17 which show cross sections D-D and C-C along the parallel longitudinal planes shown in FIG. 16.

Upon the subsequent displacement of the dosage setting means 7 towards the proximal end 3a of the body 2 of device 1, the sliding protrusion 11a moves along the slot 10a in the coupling 22. As a result, the driver 21 rotates in a clockwise direction about the pivot point 13. One of the drive pawls 14a, 14b on the driver 21, normally a drive pawl positioned behind a peak of a tooth, engages with the rear face of the tooth in the set of ratchet teeth 18a, 18b in which it is located such that the longitudinal rod is displaced upon further movement of the dosage setting means in an axial direction in order to administer a dosage of medicament.

This operation, i.e. the continued withdrawal and subsequent depression of the push button 7, serves to move the drive pawls 14a, 14b successively into subsequent valleys or spaces between the teeth and drive the drive rod 15 towards the proximal end 3a of the body 2 of device 1. After the drive pawl reaches the surface 28a, 28b after the last tooth of the drive rod 15, no further displacement can be made.

The resistance pawls 26a, 26b are fixed to the body 2 of the device 1 and serve to resist or prevent movement of the drive rod ("expelling means") 15 in a direction opposite to the administering direction, i.e. in a direction towards the proximal end 3a of the body 2 of device 1. This ensures a consistent displacement of the drive rod 15 in the proximal direction only and prevents backlash or displacement of the drive rod 15 in the distal direction.

All of the sets of ratchet teeth 18a, 18b are provided on a common side of the drive rod 15 and therefore all the resistance pawls 26a, 26b and drive pawls 14a, 14b are arranged to face a common side of the drive rod.

As the drive rod 15 is displaced in the proximal direction of the device 1, the resistance pawls 26a, 26b slide over the ratchet teeth 18a, 18b on the drive rod 15.

Figure 18B:
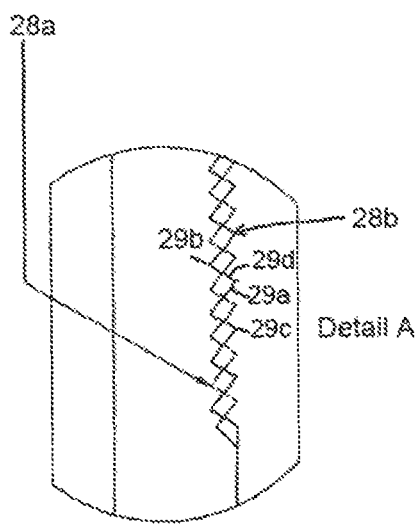
Figure 19B:
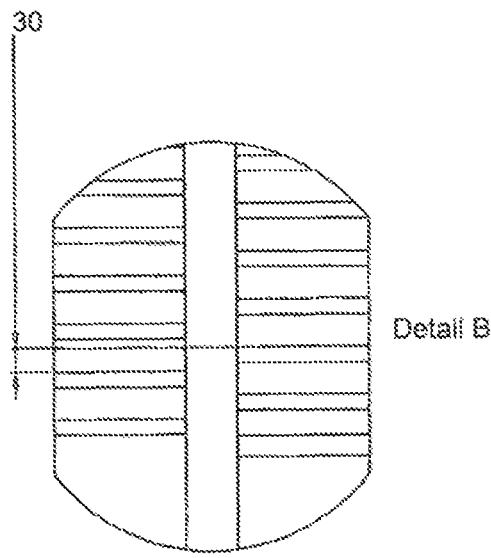
Figure 18A:
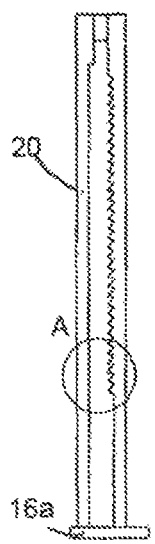
FIG. 18a shows a side view of the ratchet of the medical device as shown in FIG. 1.
Figure 19A:
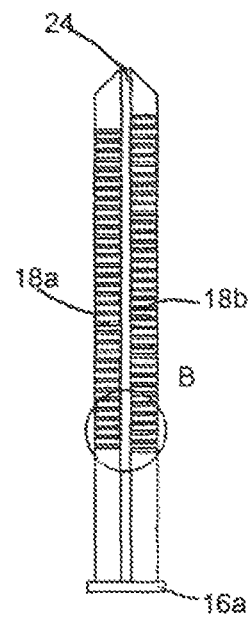
Figure 20:
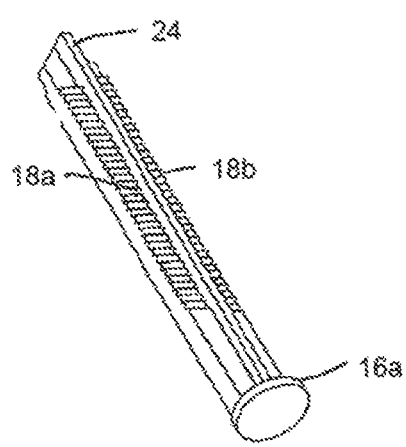

FIGS. 18a, 19a, 20, show more detailed side, plan and perspective views of a drive rod 15 having offset sets of teeth.

The drive rod 15 comprises two sets of ratchet teeth 18a, 18b separated by a divider 24. The two sets of ratchet teeth 18a, 18b are offset, i.e. engaging faces of the upper set of ratchet teeth 18a, are offset from the engaging faces of the lower set of ratchet teeth 18b in a direction parallel to the longitudinal axis of the drive rod 15. This can be more clearly seen in details A and B shown in FIGS. 18b and 19b.

As shown in FIG. 18b, each tooth has a ridge or peak 29c, a sliding front face 29a over which the pawls slide and an engagement rear face 29d as well a valley centre 29b. The teeth in each set of ratchet teeth 18a, 18b on opposing sides of the expelling means are equally spaced from one another. The offset between the two sets of ratchet teeth 18a, 18b in the embodiment is equal to half the spacing between adjacent teeth in either of the first or second sets of ratchet teeth 18a, 18b.

In the embodiments described, the upper and lower resistance pawls 26a, 26b are arranged in adjacent alignment. Similarly, the upper and lower drive pawls 14a, 14b are also arranged in adjacent alignment. Due to the offset of the two sets of ratchet teeth 18a, 18b on the drive rod 15, when driving the driver 21, as described above, during each sequence of withdrawing the push button 7 and subsequently depressing the push button 7, only one set of resistance pawl 26a and drive pawl 14a engage fully with one set of the ratchet teeth, i.e. only one of the drive pawls 14a causes the drive rod 15 to be displaced and only one of the corresponding resistance pawls 26a prevents return movement of the drive rod 15. During a subsequent sequence, the other set of drive pawl 14b and resistance pawl 26b fully engages with the other set of ratchet teeth 18b, and so on.

Accordingly, the offset of the ratchet teeth 18a, 18b provides a ratchet with finer resolution of movement, which is equal to the distance between the valley of one tooth in one of the sets of ratchet teeth 18a and the valley of an adjacent tooth in the other of the sets of ratchet teeth 18b. This offset is shown in FIG. 19b at item 30.

It follows that movement of the drive rod 15 in the embodiment described proceeds in smaller increments than if no offset were to be provided between the two sets of ratchet teeth 18a, 18b. This enables a finer dose or volume of medicament to be administered with the device 1 as a result of movement or displacement of the drive rod 15.

The offset in the case of a drive rod 15 with offset sets of ratchet teeth 18a, 18b may be adjusted according to requirements. For example, a drive rod 15 may be chosen with a larger tooth pitch in the sets of ratchet teeth in order to administer a large dosage during each cycle of movement. Conversely, a smaller pitch could be chosen. The other components however generally remain the same.

As previously mentioned, a drive rod 15 where the sets of ratchet teeth are in alignment is also envisaged. In such an embodiment, both drive pawls and resistance pawls would be in engagement with corresponding parts of teeth in each set of teeth at the same time in order to drive the expelling means and resist movement of the expelling means in the distal direction of the device.

With all of these embodiments, providing the ratchet teeth 18a, 18b on a single, common side of the drive rod 15 enables a more compact and simple device construction to be achieved.

As an alternative to offset teeth on the drive rod 15, the adjacent ratchet teeth may be aligned with the drive pawls offset from one another. Indeed, a single set of ratchet teeth can be provided which can engage with each of the drive pawls and each of the resistance pawls.

It is envisaged that other coupling mechanisms may be provided to displace the drive rod and the present invention should not be considered limited to the exemplary coupling mechanism as shown in the Figures.

Figures 21, 22:
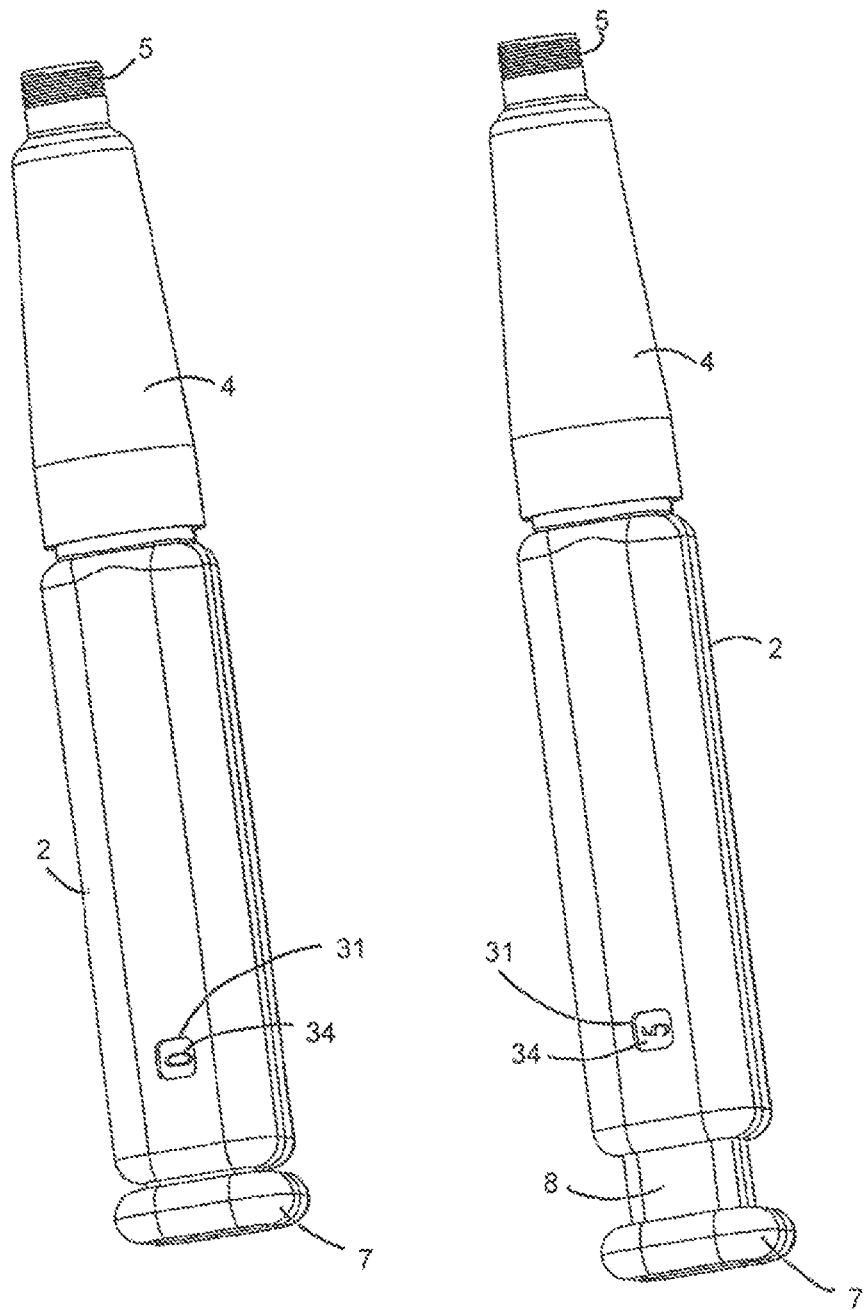
FIG. 21 shows a perspective side view of a medical device with an indicator window with a dosage button in a depressed state.
FIG. 22 shows a perspective side view of the medical device with an indicator window with the dosage button in a withdrawn state.

FIGS. 21 and 22 show a further embodiment of the device 1 having an indicator element 34 visible through a display window or aperture 31 provided in a surface of the body 2 of the device. FIGS. 21 and 22 have drive mechanisms configured to drive a drive rod 15 as described above in relation to FIGS. 1 to 20. However, the indicator element 34 and display window 31 arrangement of FIGS. 21 and 22 may be applied to devices with different drive mechanisms, including inhaler devices (not shown).

FIG. 21 shows the device 1 with the push button 7 in a depressed state. In this position of the push button 7, a first state indicator 32a of "0" provided on the indicator element 34 is visible in the window 31. This first state indicator 32a could for example indicate to a user that no dosage has been set by the push button 7.

FIG. 22 shows the device 1 with the push button 7 in a withdrawn or retracted state. In this position of the push button 7, a second state indicator 32b of "5" provided on the indicator element 34 is visible through the window 31. This second state indicator 32b could for example indicate to a user that a dosage of 5 units has been set for administration. Of course, other indications of state could be provided such as arrows or other visual or tactile markers or characters.

Figure 23:
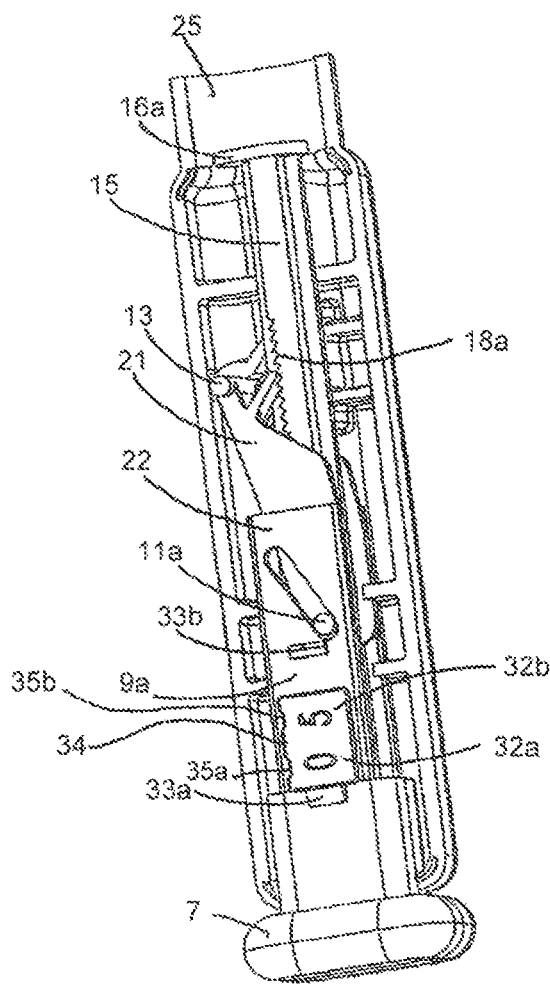
FIG. 23 shows a perspective view of the medical device shown in FIG. 21 with part of the outer body removed.

FIG. 23 shows a view of the device 1 with part of the body removed to show the internal drive mechanism and also the mechanism to move the indicator element 34. The drive mechanism includes a driver 21 rotatable about a pivot axis 13. The driver 21 includes a protrusion 11a which engages through a diagonal, linear slot in a coupling element 22. The driver 21 drives a drive rod 15 provided with sets of ratchet teeth 18a, 18b. The drive rod 15 comprises a ram 16a which can be extended or displaced through an aperture 25 in order to displace a plunger in a medicament container such an insulin cartridge (not shown). The function of such a mechanism has already been described in relation to FIGS. 1 to 20 and will not be described further here.

The coupling 22 includes a planar surface 9a, as described above. The surface 9a is provided with distal and proximal protrusions 33a, 33b, which are spaced apart a distance greater than the axial length of the indicator element 34, which is disposed in the body 2 between said protrusions 33a, 33b.

A protrusion 35c is provided along an edge of the window 31, the protrusion 35c being configured to engage with each of two spaced indents 35a, 35b located along an edge of the indicator element 34 parallel to the direction of movement of the indicator element 34. When engaged with either of the indents 35a, 35b, the protrusion 35c acts to inhibit free axial linear movement of the indicator element 34, which in this embodiment is formed as a substantially rectangular planar element.

Figure 24:
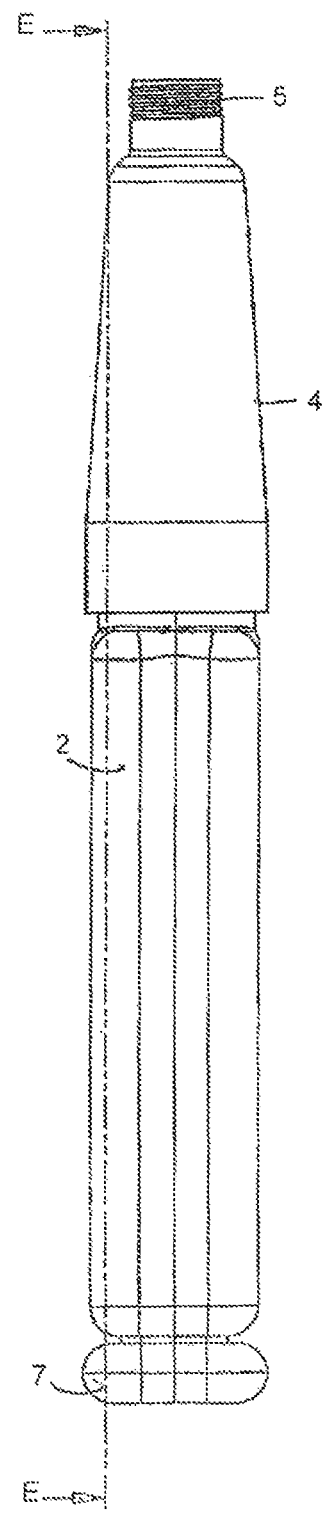
FIG. 24 shows a side view of the medical device as shown in FIG. 21 marking cross-section E-E.

The indents 35a, 35b and the protrusion 35c combine with protrusions 33a, 33b on the body 2 to form motion conversion means, the function of which will now be described with reference to FIGS. 25 to 28 which are sectional views through section E-E as shown in FIG. 24.

When the push button 7 of the device is fully depressed into the body 2 of the device, as shown in FIG. 25, the indicator element 34 is positioned with its distal edge engaged with protrusion 33a towards the rear or distal end of the device body 2. The indication "0" is shown in the window 31, represented by the dashed outline.

Upon initial withdrawal of the push button 7, as shown in FIG. 26, the indicator element 34 remains stationary relative to the body 2 of the device thanks to protrusion 35c along the edge of window 31 engaging with rearmost indent 35a of the indicator element 34. This engagement acts to resist axial movement of the indicator element 34 relative to the body 2 such that the indicator element 34 slides over the surface of the coupling 22 when during an initial movement of the push button 7 and, as there is no movement of the indicator element 34 relative to the body 2, the indication "0" remains visible to a user through window 31, indicating, for example, that the dosage has not yet been set.

Upon further withdrawal of the push button 7, as shown in FIG. 27, the proximal protrusion 33b engages with the proximal edge of the indicator element 34, which causes the indicator element 34 to be displaced in a distal axial direction of the body 2 of the device, in doing so overcoming the resistance provided by the engagement of the protrusion 35c and distal indent 35a, such that the indication "0" 32a begins to move out of visibility in the window 31.

FIG. 28 shows the fully retracted position of the push button 7. Here it can be seen that the proximal protrusion 33b on the coupling 22 maintains its engagement with the indicator element 34 thereby completing the axial movement of the indicator element 34 to bring indication "5" 32b into visibility in the display window 31. This could for example indicate to a user that the dosage has been correctly set and the push button 7 could be depressed in order to administer the dose. In this final fully withdrawn position of the push button 7, the protrusion 35c along the edge of window 31 becomes engaged with the foremost indent 35b on the edge of the indicator element 34.

Upon subsequent depression of the push button 7 in order to administer a dose, the indicator element 34 again initially remains stationary relative to the body 2 due to the resistance of protrusion 35c being engaged with the foremost indent 35b on the edge of the indicator element 34 such that the indication "5" 32b remains visible in the window 31 during an initial movement of the push button 7. This could, for example, indicate to a user that the dose has not yet been fully administered.

Similarly as when the push button 7 is withdrawn, upon continued depression of the push button 7, the distal protrusion 33a on the coupling 22 engages with the corresponding distal edge of the indicator element 34 thereby to move it in the proximal direction relative to the body 2 of the device such that the indication "0" 32a is again displayed in the window 31 and protrusion 35c again engages with rearmost protrusion 35a on the edge of the indicator element 34.

Although in the embodiment, the indicator element 34, here in the form of a sliding indicator, has been provided with indents 35a, 35b at each end of travel, it is also envisaged to provide a protrusion on the edge of the sliding indicator 34 which engages with corresponding indents provided on a corresponding edge of the window 31.

It will be understood that the mechanism provides a magnitude of displacement of the indication element 34 which is different to (i.e. less than) the magnitude of displacement of the dosage setting means. In the embodiment, the spacing of the protrusions 33a, 33b on the surface 9a of coupling 22 provides a relative or "lost motion" movement between the push button 7 and the indicator element 34. This allows the indications 32a, 32b to remain visible and unchanged during phases of the operation of the device. This can lead to improved operation of the device as the displayed indications 32a, 32b remain consistent and unchanged.

Figure 29:
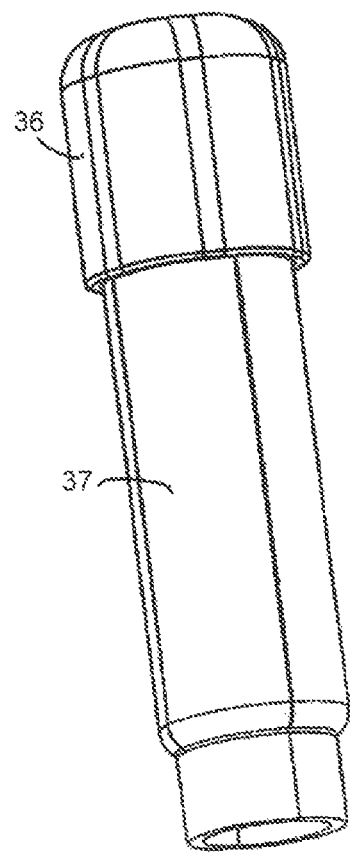
FIG. 29 shows a medical device with an alternative dosage button in a depressed state.
Figure 30:
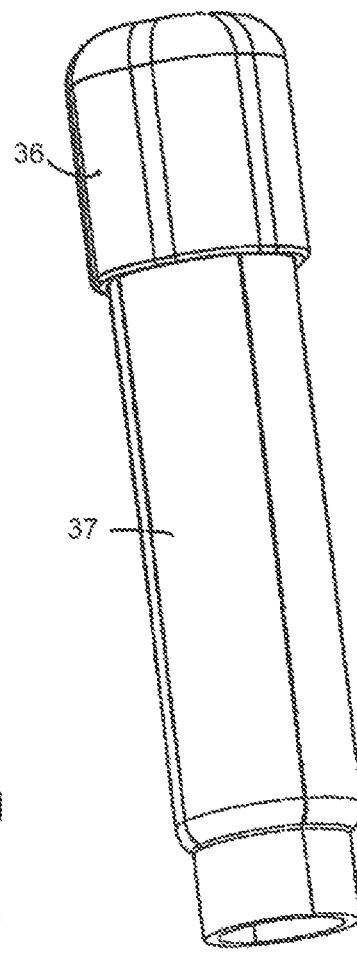
FIG. 30 shows the medical device of FIG. 29 with the dosage button in a rotated and retracted state.
Figure 31:
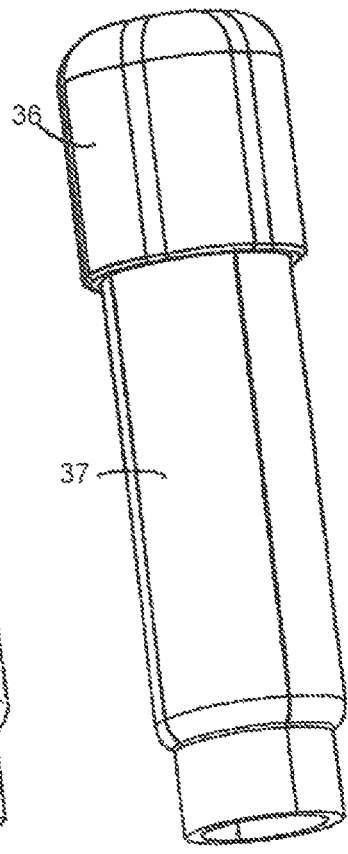
FIG. 31 shows the medical device of FIG. 29 with the dosage button in a rotated and depressed state.

While in the embodiment, an axially moveable push button 7 has been shown to provide drive of the mechanism, other forms of dosage setting means may be provided such as a dial, rotatable about the longitudinal axis of the device while still embodying the above-described arrangement of the indicator element 34. An example of such a dosage setting means with a rotating dial 36 on a cylindrical body 37 is shown in FIGS. 29 to 31 in a fully screwed in position in FIG. 29, a fully retracted, i.e. screwed-out position in FIG. 30 and a fully depressed position in FIG. 31.

A further embodiment of a device 1 is shown in FIGS. 32 to 39 comprising a different indicator element arrangement. Externally, the device 1 is formed similarly to the embodiments described above, comprising a body 2, a cartridge receiver 4, a cartridge with a threaded portion 5 for receiving an injection needle, a push button or dosage means 7 and a window or aperture 31. Through the window 31, an indication, here the number "5" is visible, which is on an indicator element 42.

Figure 32:
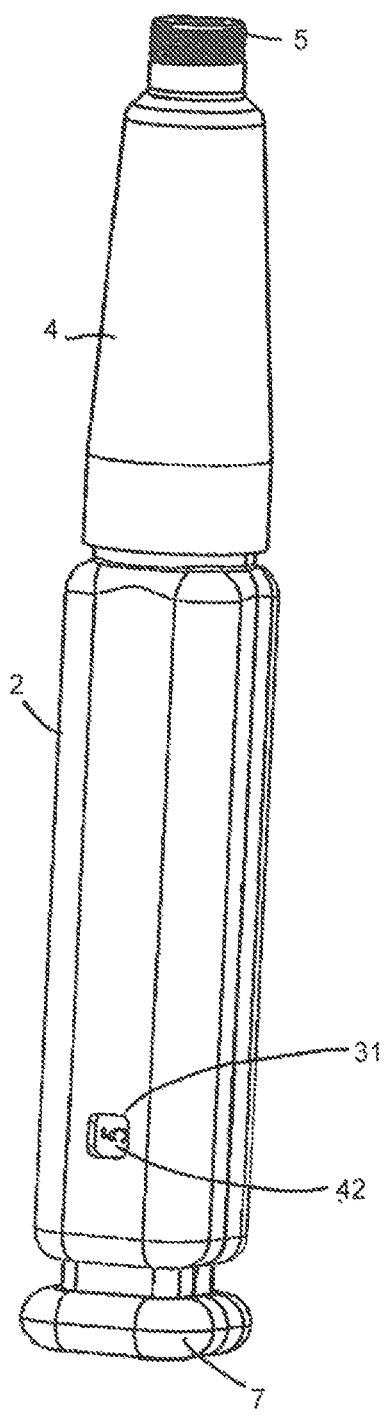
FIG. 32 shows an external perspective view of a further medical device with the dosage button in a withdrawn state.
Figure 33:
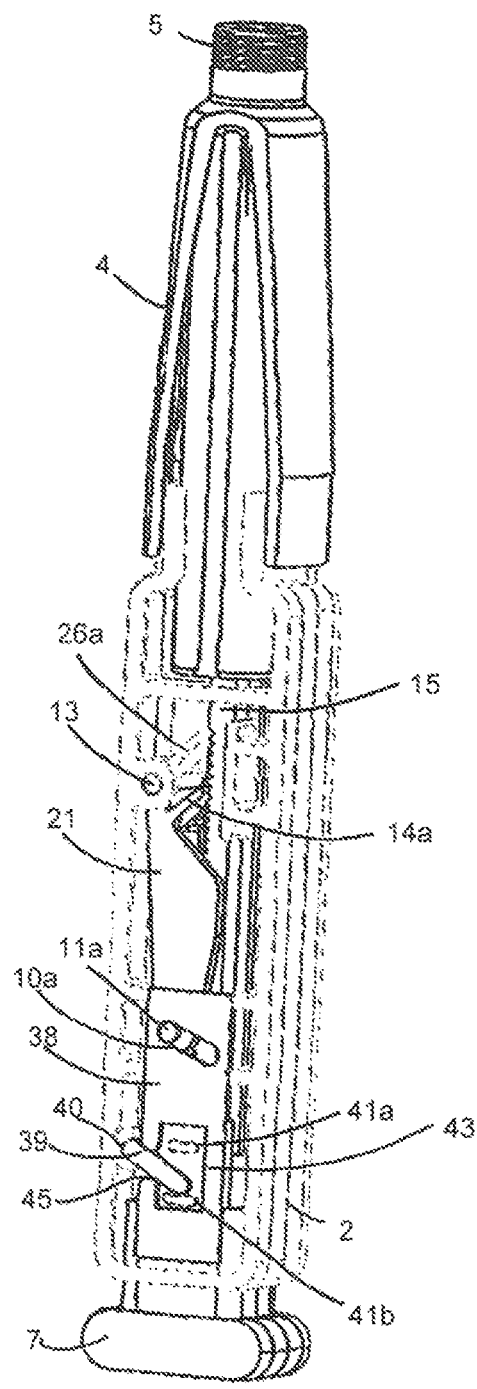
FIG. 33 shows a partial cross-section through the device as shown in FIG. 32.

FIG. 33 shows a cross-section through the device shown in FIG. 32. The dispensing mechanism is similar to that shown in FIGS. 1 to 31 and comprises a driver 21 with drive pawl 14a, 14b and resistance pawls 26a, 26b arranged to engage with ratchet teeth 18a, 18b on a drive rod 15.

A coupling element 38 is provided, which comprises a diagonal slot 10a within which a protrusion 11a is received. These parts function similarly to the coupling element 22 described in relation to FIGS. 1 to 31 in order to set a dose with the push means 7 and administer a dose. The dosage and administering functions will accordingly not be described further here.

In contrast to the device of FIGS. 1 to 31, as shown in FIG. 33, the coupling element 38 comprises a rectangular aperture 43. Along one edge of the aperture, an opening 45 is provided in which a conversion means in the form of lever 39 is positioned. The lever 39 extends through the opening 45 into the aperture 43 from a pivoted connection 40 on the body 2 located outside the aperture 43.

The indicator element 42 is provided with a pair of spaced protrusions, represented by the dashed lines 41a, 41b. The protrusions 41a, 41b extend from the rear surface or underside of the indicator element 42 (not shown in FIG. 33 or 35) and are positioned towards either end of the indicator element 42 in the longitudinal direction of the device. When assembled, the protrusions 41a, 41b extend into the aperture 43 such that they are positioned either side of the distal end of the lever 39, i.e. the end of the lever 39 furthest from the pivoted connection 40, such that the indicator element 42 rests atop the lever 39.

FIG. 33 shows the device with the push button 7 in a retracted position. Here it can be seen that the lever 39 is in contact with the rearmost or distal protrusion 41b of the indicator element 42 and is orientated such that the lever 39 is angled towards the distal end of the body 2.

Figure 34:
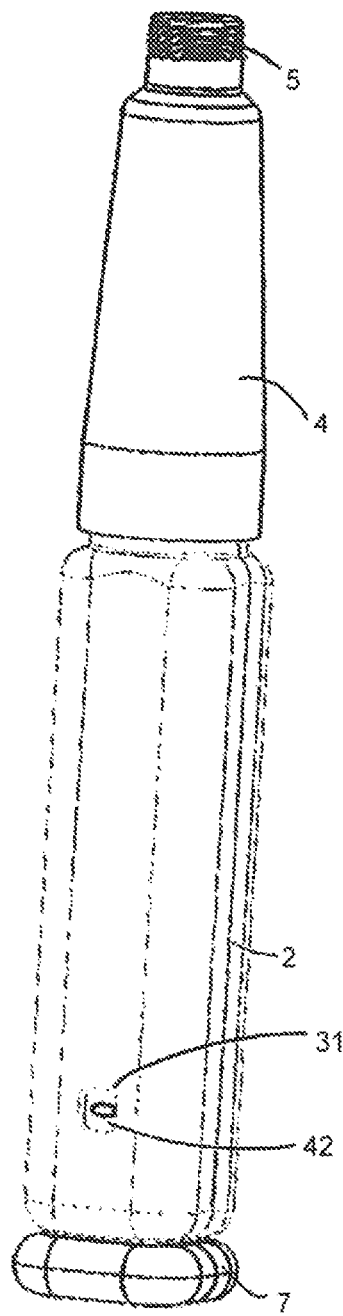
FIG. 34 shows an external perspective view of the device of FIG. 32 with the dosage button on a depressed state.

FIG. 34 shows an external view of the device of FIGS. 32 and 33 when the push button 7 is in a fully depressed position. In this position, the indicator element 42 now shows the indication "0". As has been described in relation to FIGS. 28 to 31, the indication "0" can be used to indicate to a user that no dose has been set and the indication "5" can be used to indicate that a dose of 5 units has been set, for example.

Figure 35:
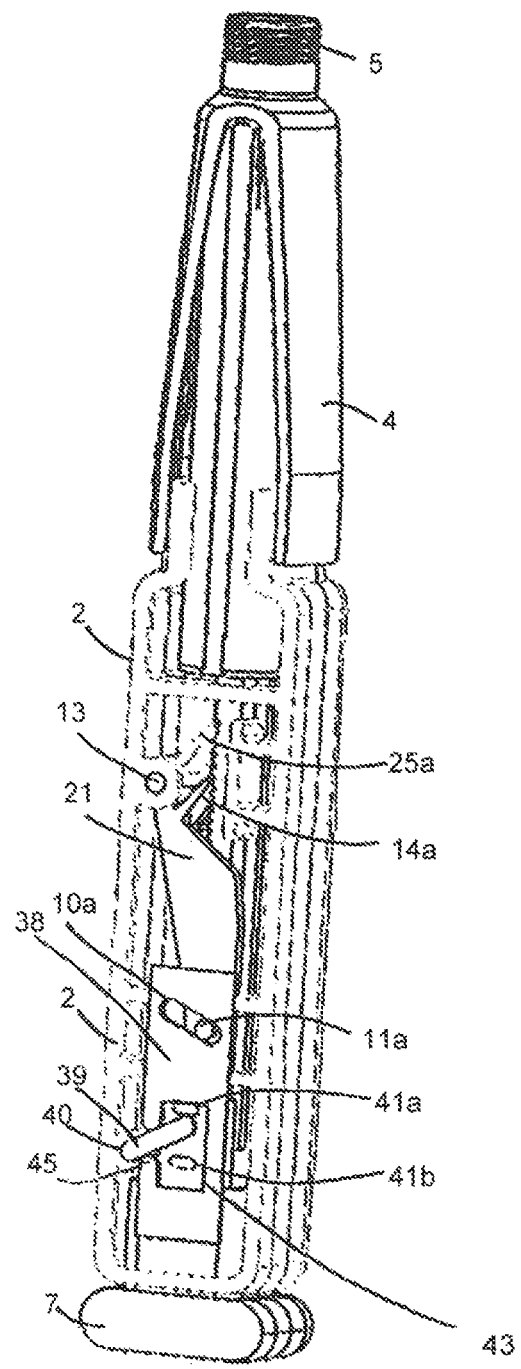
FIG. 35 shows a partial cross-section through the device as shown in FIG. 33.

As can be seen in FIG. 35, with the push button 7 in a fully depressed state, the rectangular aperture 43 has been axially displaced in the proximal direction of the device relative to the position of the rectangular aperture 43 of the device in the state shown in FIG. 33. It can be seen that the opening 45 in the side of the aperture 43 has therefore also moved in a corresponding towards the proximal end of the body 2. As the lever 39 is pivotally attached to a fixed pivot 40 on the body of the device, the movement of the aperture 43 and the opening 45 therein causes rotation of the lever 39 about the pivot 40. As the distance between the pivot 40 and the opening 45 is less than the distance between the opening 45 and the distal end of the lever 39, it can be appreciated that a movement of the aperture 43 results in a movement of the distal end of the lever 39 of a greater magnitude, which moves the indicator element 42, via the protrusions 41a, 41b, a corresponding distance. Thus it can be seen that the opening 45 acts as a fulcrum 43.

The relative lengths of the lever 39 between the pivot 40 and the fulcrum 43 and the length between the fulcrum 43 and the distal end of the lever 39, or its point of contact with the protrusions 41a, 41b of the indication element 42, may be selected to produce a desired magnitude of movement of the indication element 42 relative to the dosage setting means 7.

As shown in FIG. 35, in the depressed state of the push button 7, the distal end of the lever 39 is in contact with the protrusion 41a of the indicator element 42 towards the proximal end of the body 2 and has moved the indicator element 42 such that the indication "0" is now visible in the aperture or window 31 as shown in FIG. 34.

The lever 39 acts to convert a movement of a first magnitude of the push button 7 or coupling 38 into a movement of a second, greater magnitude of the indicator element 42. In a device with limited space, the lever 39 can provide a greater movement and functionality of the indicator element 42 than if the movement of the indicator element 42 was limited only to the same magnitude or degree of movement of the push button 7. For example, a 4 mm movement of the indicator element 42 can result from just a 2 mm axial movement of the push button 7, thereby providing a "gained motion" effect.

It will be understood however, that the opening 45 or fulcrum 43 and lever 39 may be arranged with a shorter distance between the opening 45 and the distal end of the lever 39 than the distance between the pivoted end 40 of the lever 39 and the opening 45 such that a smaller magnitude of movement of the indicator element 42 is achieved relative to the magnitude of movement of the push button 7.

As a further alternative, the lever 39 may be formed of a resiliently flexible material such that when the indicator element 42 reaches the limit of its movement, if the lever 39 should be caused to rotate further, for example if the manufacturing tolerances of the lever 39 are such that it is slightly longer or wider than necessary or if the fulcrum 43 or opening 45 position is not precisely located, the lever 39 will flex to prevent damage to itself or to the indicator element 42.

Figure 36:
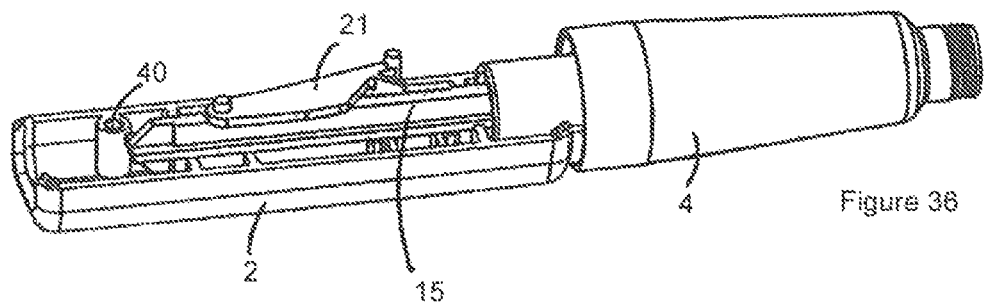
FIGS. 36 to 39 show the medical device of FIGS. 32 and 33 in partial stages of assembly.

FIGS. 36 to 39 show some assembly steps of the device with the lever. FIG. 36 shows the body, driver 21 and drive rod 15 located in the body 2. The body 2 is formed with a circular aperture 40 for receiving a support 44 of the lever 39.

Figure 37:
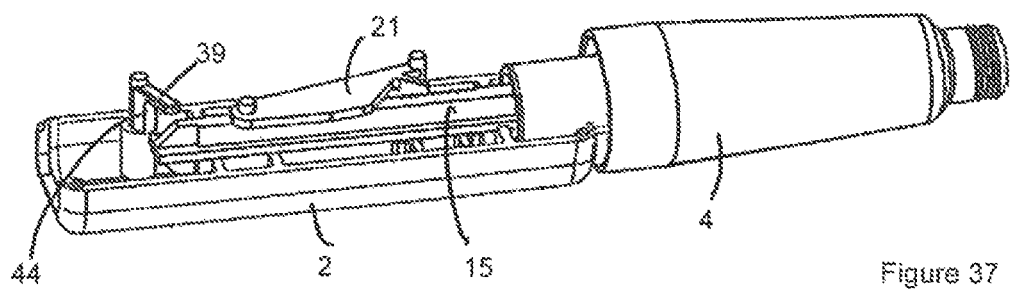

FIG. 37 shows the support 44 of the lever 39 located in the aperture 40. The lever 39 is pivotable about the axis of the circular aperture 44. Although shown in FIG. 37 as a separate part in the embodiment, the lever 39 could be formed integrally with the body 2, yet still able to pivot.

Figure 38:
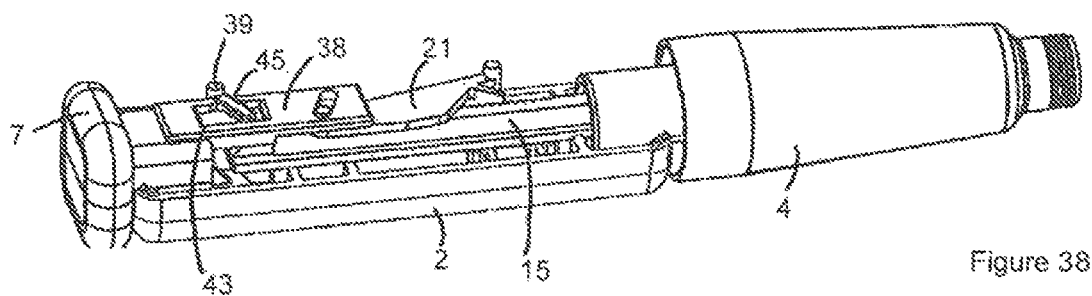

FIG. 38 shows the device with the coupling 38 attached to the push button 7 fitted. The lever 39 can be seen located in the opening 45 provided along one longitudinal side of the rectangular aperture 43.

Figure 39:
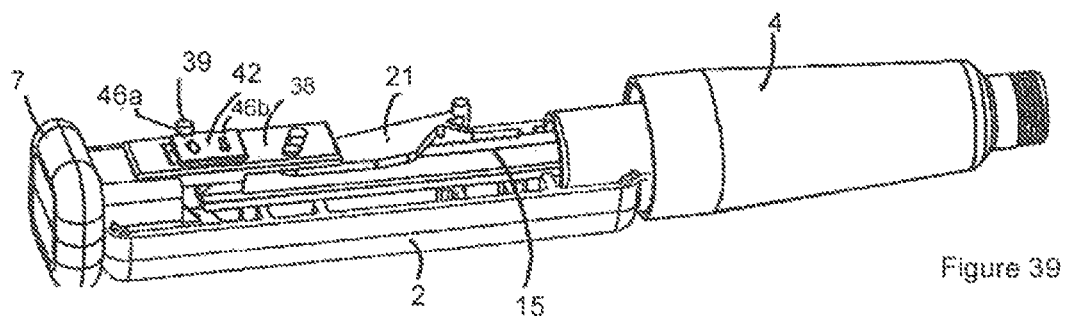

Finally, FIG. 39 shows the indicator element 42 positioned atop the coupling 38 and hence lever 39. The indicator element 42 is formed with the lever-engagable protrusions 41a, 41b underneath, which were shown and described in relation to FIGS. 33 and 35.

The indicator element 42 is shown provided with indents 46a, 46b, which have a similar function to the indents 35a, 35b described in relation to FIGS. 23 and 25 to 28 to resist free motion of the indicator element 42.

Although not shown in the Figures, it is envisaged that instead of a lever 39, the conversion means could comprise geared or threaded components, with the gearing or threading being chosen or configured such that a predetermined magnitude of movement of the indicator element 34 is achieved for a predetermined differing magnitude of movement of the push button 7.

In each of the aforementioned embodiments, the dosage setting means 7 could be indirectly or directly coupled to the indication element 34, 42. The indicator element 34, 42 is typically constrained within a channel or guide elements to limit the lateral movement thereof.

FIG. 40 shows an alternative dispensing mechanism provided in a device 1. The device 1 includes a medicament container in the form of a cartridge receptacle 4. Within the cartridge receptacle 4, a cartridge is contained with a screw thread 5 at the proximal end to receive a needle.

Similarly to the embodiments shown in FIGS. 1 to 39, the dispensing mechanism comprises a dosage setting means in the form of a push button 7. The dosage setting means is formed with a shaft 8 connecting the push button 7 with a plate 38 in which a diagonal slot 52a is formed similarly to the embodiments of FIGS. 1 to 39. Accordingly, this aspect of the embodiment will not be described in further detail.

An expelling means 51 is provided in the form of a ram with a circular disc 52 to engage with the plunger of a cartridge in order to dispense a liquid medicament therefrom.

A drive element 48 is provided. The drive element 48 comprises an arm 48a connected towards the proximal end thereof to a pivot point 49 formed in the body 55 of the mechanism. At the distal end of the drive element of driver, a circular protrusion or follower 52a is provided which engages with the diagonal slot 10a in the plate 38 of the dosage setting means 7.

The drive element 48 comprises a further pair of arms 48b which extend from the distal end of the driver 48 in the proximal direction of the mechanism and device and angled relative the arm 48a connected to the pivot point 49. Each of the pair of arms 48b comprises at their proximal, free ends, a drive pawl 48c.

The expelling means 51 comprises a rack of teeth 54 which are formed to engage with the teeth 47c of a drive wheel 47. The drive wheel 47 has a central section 47c formed as a gear wheel which engages with the teeth 54 of the rack of the expelling means 51.

The drive wheel 47 is formed with two ratchet wheels 47a, 47b at either end. The ratchet wheels 47a, 47b have a larger diameter to the diameter of the central gear wheel 47c. The teeth of the ratchet wheels are offset relative to one another, i.e. the faces of the teeth in one ratchet wheel are offset from the faces of the teeth in the other ratchet wheel. Similarly to the embodiments described in relation to FIGS. 1 to 39, this can provide a finer movement and thus dosage.

Biasing pawls 50 are formed with the body 55 and are angled in the proximal direction of the device. Two such biasing pawls are provided. One upper biasing pawl engages with one of the ratchet wheels 47a and the other, lower biasing pawl engages with the other of the ratchet wheels 47b. It can therefore be seen that these biasing pawls 50 serve to prevent anticlockwise (as seen in FIGS. 40m, 41) rotation of the drive wheel and can therefore be seen to act similarly to the biasing pawls described in relation to FIGS. 1 to 39. The biasing pawls 50 face a common side of the ratchet wheels provided on the drive wheel.

FIG. 40 shows the device 1 with the push button 7 in a depressed position. As can be seen from FIGS. 40 and 41, upon withdrawal of the push button 7 into the withdrawn position as shown in FIG. 41, the protrusion 52a on the driver 48 follows the diagonal slot 10a such that the driver 48 is caused to rotate anticlockwise about the pivot point 49. In so doing, the drive pawls 48c slide over the teeth in the ratchet wheels 47a, 47b, thus moving into successive valleys formed by the ratchet teeth. The biasing pawls 50 prevent rotation of the drive wheel in an anticlockwise direction during this movement of the drive pawls.

Upon the subsequent depressing of the push button 7 in the axial proximal direction, the driver 48 is caused to rotate about the pivot point 49. Due to the offset of the ratchet teeth in the ratchet wheels 47a, 47b, only one of the drive pawls 48c engages fully with an engaging face of one of the ratchet wheels 47a, 47b and rotates the ratchet wheel 47 about its axis 56 in a clockwise direction as viewed in FIG. 41.

As the drive wheel 47 rotates, the gear teeth 47c, which are engaged with the rack of teeth 54 on the expelling means 51, rotate causing the expelling means to be displaced in an axial direction to deliver or administer a dose from the cartridge.

FIG. 42 shows the expelling means 51, driver 48 and drive wheel 47. Due to the larger relative diameters of the ratchet wheels 47a, 47b to the size of the gear wheel 47c on the drive wheel 47, the expelling means sits between the drive arms 48c of the driver 48. This again allows for a more compact arrangement of components.

FIG. 43 shows a view of the drive wheel 47. Each ratchet wheel 47a, 47b shares the same axis of rotation as the central gear wheel 47c located therebetween. The ratchet wheels 47a, 47b may be formed integrally with the gear wheel 47c.

As with the embodiments of FIGS. 1 to 39, the drive pawls could be offset rather than the ratchets on the drive wheel, with the ratchets of the drive wheel being in alignment.

Various modifications may be made to the embodiments described without departing from the scope of the invention as defined in the accompanying claims. Furthermore, a skilled person will note that, though the terms "upper" and "lower" are used throughout the description for ease of reference to the figures, these terms are interchangeable with other differentiating terms for similar or identical features such as "first" and "second", for example.

The invention claimed is:

1. A dispensing mechanism for administering a dosage of a medicament, the mechanism comprising:
    a housing;
    a dosage setting element for setting a single dose of the medicament to be administered from a cartridge containing multiple dosages of the medicament, the dosage setting element being moveable axially by a user in a first direction for setting the dose and moveable axially by a user in a second direction for administering the dose; and
    an indication element to indicate a set dose of the medicament, the indication element being arranged to be displaced axially and linearly relative to said housing by a predetermined movement of the dosage setting element, the indication element being rotationally fixed relative to the housing; and
    wherein the dispensing mechanism further includes a conversion element configured, during linear displacement of the indication element relative to the dosage setting element, to convert a linear movement of the dosage setting element of a first magnitude relative to said housing into a linear movement of the indication element of a second magnitude relative to said housing, and wherein said first magnitude of linear movement is different from said second magnitude of linear movement.

2. The dispensing mechanism as claimed in claim 1, wherein the first magnitude of movement is greater than the second magnitude of movement.

3. The dispensing mechanism as claimed in claim 1, wherein the first magnitude of movement is smaller than the second magnitude of movement.

4. The dispensing mechanism as claimed in claim 1, wherein the conversion element is configured to move the indication element during all movement of the dosage setting element.

5. The dispensing mechanism as claimed in claim 1, wherein the conversion element comprises a lever.

6. The dispensing mechanism as claimed in claim 5, wherein the lever is configured to act about a fulcrum provided by the dosage setting element.

7. The dispensing mechanism as claimed in claim 5, wherein the lever is resiliently flexible.

8. The dispensing mechanism as claimed in claim 5, wherein the lever is pivotally attached to said housing.

9. The dispensing mechanism as claimed in claim 5, wherein the lever is formed integrally with said housing.

10. The dispensing mechanism as claimed in claim 1, wherein the indication element is movable within a guide channel.

11. The dispensing mechanism as claimed in claim 1, wherein the indication element is slidingly supported in, on, or by the housing.

12. The dispensing mechanism as claimed in claim 1, further comprising a resisting element arranged to resist movement of the indication element relative to movement of the dosage setting element.

13. The dispensing mechanism as claimed in claim 12, wherein the resisting element comprises a protrusion receivable in one or more corresponding recesses.

14. The dispensing mechanism as claimed in claim 1, wherein the dispensing mechanism includes an aperture through which at least a portion of the indication element is exposed to a user.

15. The dispensing mechanism as claimed in claim 1, wherein the indication element comprises at least one of tactile and visual indications.

16. The dispensing mechanism as claimed in claim 1, wherein the indication element is moved directly by the dosage setting element.

17. The dispensing mechanism as claimed in claim 1, wherein the indication element is moved indirectly by the dosage setting element.

18. The dispensing mechanism as claimed in claim 1, wherein the indication element is further rotationally fixed relative to the dosage setting element.

19. A medical device comprising the dispensing mechanism according to claim 1.

* * * * *